(12) United States Patent
Marquis et al.

(10) Patent No.: US 7,901,679 B2
(45) Date of Patent: Mar. 8, 2011

(54) HUMANIZED ANTI-GHRELIN ANTIBODIES

(75) Inventors: David Matthew Marquis, Encinitas, CA (US); Eric Michael Smith, San Diego, CA (US); Danise Rogers Subramaniam, Zionsville, IN (US); Derrick Ryan Witcher, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 303 days.

(21) Appl. No.: 12/278,419

(22) PCT Filed: Feb. 21, 2007

(86) PCT No.: PCT/US2007/062459
§ 371 (c)(1),
(2), (4) Date: Aug. 6, 2008

(87) PCT Pub. No.: WO2007/101021
PCT Pub. Date: Sep. 7, 2007

(65) Prior Publication Data
US 2009/0181018 A1 Jul. 16, 2009

Related U.S. Application Data

(60) Provisional application No. 60/775,723, filed on Feb. 22, 2006.

(51) Int. Cl.
*C07K 16/00* (2006.01)
*C12P 21/08* (2006.01)
*A61K 39/395* (2006.01)
*A61K 39/00* (2006.01)

(52) U.S. Cl. ............... 424/133.1; 424/130.1; 424/145.1; 530/387.1; 530/387.9; 530/388.24

(58) Field of Classification Search .................. None
See application file for complete search history.

(56) References Cited

FOREIGN PATENT DOCUMENTS

| WO | WO 01/78335 | 10/2001 |
|----|-------------|---------|
| WO | WO 2005/016951 | 2/2005 |
| WO | WO 2005/026211 | 3/2005 |
| WO | WO 2006/019577 | 2/2006 |

OTHER PUBLICATIONS

Wren et al., Ghrelin Causes Hyperphagia and Obesity in Rats. Diabetes, Nov. 2001, vol. 50, pp. 2540-2547.*
Cummings et al., Elevated Plasma Ghrelin Levels in Prader-Willi Syndrome. Nature Medicine, Jul. 2002, vol. 8, pp. 643-644.*
Moran et al., Ghrelin and Measures of Satiety Are Altered in Polycystic Ovary Syndrome But Not Differentially Affected by Diet Composition. The Journal of Clinical Endocrinology and Metabolism, Jul. 2004, vol. 89, pp. 3337-3344.*
Cigaina et al., Plasma Ghrelin and Gastric Pacing in Morbidly Obese Patients. Metabolism Clinical and Experimental, 2007, vol. 56, pp. 1017-1021.*
Kusaka et al., Metformin, But Not Pioglitazone, decreases Postchallenge Plasma Ghrelin Levels in Type 2 Diabetic Patients: A Possible Role in Weight Stability? Diabetes, Obesity and Metabolism, Published Online: Mar. 18, 2008, pp. 1-8.*
Bednarek, et al., "Structure-function studies on the new growth hormone-releasing peptide, ghrelin: Minimal sequence of ghrelin necessary for activation of growth hormone secretagogue receptor 1a," *Journal of Medicinal Chemistry* 43(23):4370-4376 (2000).
Davies, et al., "Affinity improvement of single antibody VH domains: residues in all three hypervariable regions affect antigen binding," *Immunotechnology*, 2(3):169-179.
Gaytan, et al. "Immunolocalization of Ghrelin and Its Functional Receptor, the Type 1A Growth Hormone Secretagogue Receptor, in the Cyclic Human Ovary," *Journal of Clinical Endocrinology and Metabolism*, 88(2):879-887 (2003).
Helmling, et al., "The Promise of Ghrelin Antagonism in Obesity Treatment," *Drug News and Perspectives*, 19(1):13-20 (2006).
Holt, et al., "Domain antibodies: proteins for therapy," *Trends in Biotechnology*, 21(11):484-490 (2003).
Hosoda, et al., "Structural divergence of human ghrelin identification of multiple ghrelin-derived molecules produced by post-translational processing," *Journal of Biological Chemistry*, 278(1):64-70 (2003).
Murakami, et al., "Role for central ghrelin in food intake and secretion profile of stomach ghrelin in rats," *Journal of Endocrinology* 174(2):283-288 (2002).
Murata, et al., "Ghrelin modulates the downstream molecules of insulin signaling in hepatoma cells," *Journal of Biological Chemistry* 277(7):5667-5674 (2002).
Yoshihara, et al., "Ghrelin: A Novel Peptide for Growth Hormone Release and Feeding Regulation," *Current Opinion in Clinical Nutrition and Metabolic Care*, 5(4):391-395 (2002).

* cited by examiner

*Primary Examiner* — Sharon Wen
(74) *Attorney, Agent, or Firm* — Andrea M. Castetter

(57) ABSTRACT

Provided are humanized monoclonal antibodies, and antigen-binding portions thereof, which bind acylated and unacylated human ghrelin. Such antibodies are useful for neutralizing ghrelin activity and treating disorders in which ghrelin activity is detrimental, including obesity and related disorders, and various cancers.

4 Claims, No Drawings

HUMANIZED ANTI-GHRELIN ANTIBODIES

This application is a national stage entry of PCT/US07/62459 which claims priority from provisional application U.S. Ser. No. 60/775,723 filed Feb. 22, 2006.

Human ghrelin is a 28 amino acid peptide hormone having the amino acid sequence GSSFLSPEHQRVQQRKESKKP-PAKLQPR (SEQ ID NO: 1) that circulates in the blood. When acylated at the serine at amino acid position three (Ser$^3$) with an n-octanoyl group ("C8" or "C8 acylated ghrelin"), it binds the growth hormone secretagogue receptor (GHS-R1a) in the pituitary, resulting in release of growth hormone. Ghrelin serum levels increase during food deprivation in animals, peak prior to eating, and decrease upon refeeding. Persons with Prader-Willi syndrome, a genetic disorder that causes severe obesity with uncontrollable appetite, have extremely high levels of ghrelin. These observations indicate that ghrelin plays a key role in motivating feeding.

In addition to its role in eating disorders, ghrelin has also been shown to have a proliferative effect in the HepG2 hepatoma cell line and in prostate cancer cell lines. The growth of other cell types including, for example, H9c2 cardiomyocytes, pancreatic adenocar-cinoma, adrenal cells, pituitary somatotroph cells, adipocytes, osteoblastic cells, breast cancer cell lines, etc., is also enhanced by ghrelin.

Thus, agents that modulate the activity of ghrelin represent possible treatments for various diseases or disorders in mammals, for example obesity and obesity-related disorders such as non-insulin dependent diabetes mellitus, as well as certain cancers, wherein a decrease in ghrelin level or activity contributes to a desirable therapeutic effect.

PCT International Publication No. WO 2006/019577 (PCT/US2005/023968) discloses the Fab portions of several murine monoclonal antibodies to the C-terminal end of human ghrelin, designated therein as Fabs 3281, 4731, and 4281 ("murine D4 Fabs"). These Fabs bind both the acylated and unacylated forms of human ghrelin at an antigenic epitope located within amino acids 14-27 of this peptide. The affinity ($K_D$) of these Fabs for full length (1-28), C8 acylated human ghrelin is in the range from $4.36 \times 10^{-9}$ to $8.62 \times 10^{-11}$ M (4360 pM to 86.2 pM).

There is a pressing need for safe and effective means to treat obesity, obesity-related disorders and diseases, other eating disorders, and disorders that correlate with elevated ghrelin levels. Due to its role in inducing feeding, and its proliferative effects on certain cell lines, ghrelin is a desirable target for such therapeutic intervention. The humanized monoclonal antibodies and antigen-binding portions thereof disclosed herein exhibit ranges and particular combinations of binding and biological properties, i.e., $K_D$, $k_{on}$, and $k_{off}$ for acylated and des-acyl human ghrelin, and $IC_{50}$ values in inhibiting acylated human ghrelin mediated increase in intracellular calcium in hamster AV12 cells stably transfected to express human ghrelin receptor GHS-R1a, unlike those of the murine D4 Fabs disclosed in International application PCT International Publication No. WO 2006/019577 (PCT/US2005/023968). These properties facilitate selection of optimal antibody agents for the therapeutic applications encompassed by this invention.

Accordingly, in a first aspect, the present invention provides a humanized monoclonal antibody, or antigen-binding portion thereof, that specifically binds both acylated and des-acyl human ghrelin, and that:

a) exhibits an equilibrium dissociation constant, $K_D$, in the range of from about 1730 pM to about 11 pM for acylated human ghrelin, b) exhibits a $k_{on}$ value in the range of from about $4.44 \times 10^6$ l/Ms to about $4.89 \times 10^7$ l/Ms for acylated human ghrelin, and c) exhibits a $k_{off}$ value in the range of from about $4.98 \times 10^{-5}$ l/s to about $2.58 \times 10^{-2}$ l/s for acylated human ghrelin, wherein said $K_D$, $k_{on}$ and $k_{off}$ values are determined by surface plasmon resonance; and d) inhibits acylated human ghrelin mediated increase in intracellular calcium in hamster AV12 cells stably transfected to express human growth hormone secretagogue receptor 1a with an $IC_{50}$ of about 10 nM or less, about 5 nM or less, about 2.5 nM or less, or about 1 nM or less as measured by an in vitro FLIPR calcium assay.

In another aspect, the humanized monoclonal antibody or antigen-binding portion thereof of can comprise a heavy chain constant region selected from human IgG1, IgG2, IgG3, and IgG4, or a light chain constant region selected from human kappa or lambda. Human IgG1 and IgG4 are preferred.

In another aspect, the humanized monoclonal antibody or antigen-binding portion thereof can comprise a heavy chain constant region selected from human IgG1, IgG2, IgG3, and IgG4, and a light chain constant region selected from human kappa or lambda. Human IgG1 and IgG4 are preferred.

In another aspect, the humanized antigen-binding portion is selected from the group consisting of a Fab fragment, a F(ab')$_2$ fragment, and a single chain Fv fragment.

In another aspect, any one of the preceding humanized monoclonal antibodies or antigen-binding portions thereof can be one wherein: the light chain variable region comprises a peptide with the sequence shown in SEQ ID NO:4 and the heavy chain variable region comprises a peptide with the sequence shown in SEQ ID NO:5; the light chain variable region comprises a peptide with the sequence shown in SEQ ID NO:32 and the heavy chain variable region comprises a peptide with the sequence shown in SEQ ID NO:45; the light chain variable region comprises a peptide with the sequence shown in SEQ ID NO:33 and the heavy chain variable region comprises a peptide with the sequence shown in SEQ ID NO:46; the light chain variable region comprises a peptide with the sequence shown in SEQ ID NO:34 and the heavy chain variable region comprises a peptide with the sequence shown in SEQ ID NO:47; the light chain variable region comprises a peptide with the sequence shown in SEQ ID NO:35 and the heavy chain variable region comprises a peptide with the sequence shown in SEQ ID NO:48; the light chain variable region comprises a peptide with the sequence shown in SEQ ID NO:36 and the heavy chain variable region comprises a peptide with the sequence shown in SEQ ID NO:49; the light chain variable region comprises a peptide with the sequence shown in SEQ ID NO:37 and the heavy chain variable region comprises a peptide with the sequence shown in SEQ ID NO:50; the light chain variable region comprises a peptide with the sequence shown in SEQ ID NO:38 and the heavy chain variable region comprises a peptide with the sequence shown in SEQ ID NO:51; the light chain variable region comprises a peptide with the sequence shown in SEQ ID NO:39 and the heavy chain variable region comprises a peptide with the sequence shown in SEQ ID NO:52; the light chain variable region comprises a peptide with the sequence shown in SEQ ID NO:40 and the heavy chain variable region comprises a peptide with the sequence shown in SEQ ID NO:53; the light chain variable region comprises a peptide with the sequence shown in SEQ ID NO:41 and the heavy chain variable region comprises a peptide with the sequence shown in SEQ ID NO:54; the light chain variable region comprises a peptide with the sequence shown in SEQ ID NO:42 and the heavy chain variable region comprises a peptide with the sequence shown in SEQ ID NO:55; the light chain variable region comprises a peptide with the sequence shown in SEQ ID NO:43 and the heavy chain variable region comprises a peptide with the sequence shown in SEQ ID NO:56; or the light chain variable region comprises a peptide with the sequence shown in SEQ ID NO:44 and the heavy chain variable region comprises a peptide with the sequence shown in SEQ ID NO:57.

In another aspect, the present invention provides a pharmaceutical composition, comprising any one of the foregoing humanized monoclonal antibodies or antigen-binding portions thereof, and a pharmaceutically acceptable carrier, diluent, or excipient.

In another aspect, the present invention provides a humanized monoclonal antibody or antigen binding portion thereof as described above for use as a medicament.

In another aspect, the present invention provides the use of a humanized monoclonal antibody or antigen-binding portion thereof as described above for the manufacture of a medicament for the treatment of a disease or disorder selected from the group consisting of obesity, non-insulin dependent diabetes mellitus, Prader-Willi syndrome, hyperphagia, impaired satiety, or cancer in a mammal, preferably a human.

In another aspect, the present invention provides a method of treating obesity, non-insulin dependent diabetes mellitus, Prader-Willi syndrome, hyperphagia, impaired satiety, or a cancer in a human, comprising administering to a human in need thereof an effective amount of a humanized monoclonal antibody or antigen-binding portion thereof as described above. The method of treating obesity can be either therapeutic or non-therapeutic, e.g., cosmetic or aesthetic.

In a further aspect, the present invention provides a method of neutralizing or inhibiting ghrelin activity, whether that activity results from acylated ghrelin or des-acyl ghrelin (or both), or decreasing active ghrelin levels, in a human in need thereof, comprising administering to said human an effective amount of a humanized monoclonal antibody or antigen-binding portion thereof as described above. The method of neutralizing or inhibiting ghrelin activity can be either therapeutic or non-therapeutic, e.g., also for cosmetic or aesthetic purposes.

Further scope of the applicability of the present invention will become apparent from the detailed description and examples provided below, which are given for the purpose of non-limiting illustration only.

The present invention provides humanized monoclonal antibodies, and antigen-binding portions thereof, against human ghrelin for therapeutic use in which protein engineering is used to reduce the amount of foreign protein sequence by swapping rodent antibody constant regions and variable-domain framework regions with sequences found in human antibodies.

The humanized monoclonal antibodies and antigen-binding portions thereof disclosed herein exhibit a range of dissociation constants (affinities or $K_D$s) for human acyl and des-acyl ghrelin, including unique combinations of $k_{on}$ and $k_{off}$ values, and a variety of $IC_{50}$ values in inhibiting acylated human ghrelin mediated increase in intracellular calcium in hamster AV12 cells stably transfected to express human ghrelin receptor GHS-R1a, unlike those of the murine D4 Fabs disclosed in International application PCT International Publication No. WO 2006/019577 (PCT/US2005/023968). The ranges and particular combinations of binding and biological properties, i.e., $K_D$, $k_{on}$, $k_{off}$, and $IC_{50}$ values, of the present antibodies and fragments facilitate selection of optimal antibody agents for the therapeutic applications encompassed by this invention.

Anti-ghrelin monoclonal antibodies of the invention may be useful for the treatment or prevention of obesity, obesity-related disorders, NIDDM (Type II diabetes), Prader-Willi syndrome, eating disorders, hyperphagia, impaired satiety, anxiety, gastric motility disorders (including, e.g., irritable bowel syndrome and functional dyspepsia), insulin resistance syndrome, metabolic syndrome, dyslipidemia, atherosclerosis, hypertension, hyperandrogenism, polycystic ovarian syndrome, various cancers, and cardiovascular disorders. Additionally, anti-ghrelin monoclonal antibodies of the present invention may be useful for the treatment or prevention of any disease or disorder which benefits from lower levels or lower activity of either the acylated or unacylated forms of ghrelin, or both.

The present humanized anti-ghrelin antibodies (including antigen-binding portions thereof) are capable of specifically binding to human ghrelin. Preferred anti-ghrelin antibodies are capable of modulating a biological activity associated with ghrelin, and thus are useful in the treatment or prevention of various diseases and pathological conditions, including obesity and obesity-related diseases.

The term "acylated human ghrelin" includes the 28-amino acid peptide having the sequence shown in SEQ ID NO:1, octanoylated at $Ser^3$; octanoyl ghrelin (1-27); decanoyl ghrelin (1-28); decanoyl ghrelin (1-27); and decenoyl ghrelin (1-28). Des-acyl ghrelin (1-28) and des-acyl ghrelin (1-27) do not bind growth hormone secretagogue receptor 1a. All of these molecular forms of ghrelin are found in human plasma as well as in the stomach. It is presumed that the monoclonal antibodies and antigen-binding portions thereof of the present invention specifically bind to full-length (1-28) and truncated forms of acylated human ghrelins, for example 1-27, whether containing a $Ser^3$ n-octanoyl, n-decanoyl, or n-decenoyl group, or other fatty acid, or des-acyl ghrelin.

The term "antigen-binding portion" or "antigen-binding fragment" refers to a portion of an antibody molecule that contains amino acid residues that interact with an antigen and confer on the antibody its specificity and affinity for the antigen. This antibody portion includes the "framework" amino acid residues necessary to maintain the proper conformation of the antigen-binding residues. The CDRs of the antigen-binding region of the present monoclonal antibodies are humanized versions of CDRs of murine or substantially murine origin. Examples of antibody fragments include Fab, Fab', F(ab')2, and Fv fragments; diabodies; single chain antibody molecules; and multispecific antibodies formed from antibody fragments.

The term "specific binding" or "specifically binds" as used herein refers to the situation in which the antibody, or antigen-binding portion thereof, will not show any significant binding (i.e., less than about 10%, 9%, 8%, 7%, 6%, 5%, 4%, 3%, 2% or 1%) to molecules other than its specific binding partner(s), a peptide comprising the antigenic epitope. The term is also applicable where, e.g. an antigen-binding domain of an antibody of the invention is specific for a particular epitope that is comprised by a number of antigens, in which case the specific antibody carrying the antigen-binding domain will be able to bind to the various antigens comprising the epitope. The monoclonal antibodies of the invention selectively bind to ghrelin molecules comprising SEQ ID NO: 1 and variants thereof as discussed above, and will not bind (or will bind weakly) to non-ghrelin proteins.

The terms "biological property," "biological characteristic," "biological activity," or "bioactivity," in reference to an antibody of the present invention are used interchangeably, and include, but are not limited to, the ability of such antibodies to modulate one or more activities of acylated or des-acyl ghrelin, ghrelin levels, or ghrelin activation, including, for example, change in intracellular calcium levels in at least one type of mammalian cell; in epitope/antigen affinity and specificity (e.g., anti-ghrelin monoclonal antibody binding to ghrelin); ability to antagonize an activity of acylated or des-acyl ghrelin in vivo, in vitro, or in situ (e.g., growth hormone release); the in vivo stability of the antibody; and the immunogenic properties of the antibody. The aforementioned properties or characteristics can be observed or measured using art-recognized techniques including, but not limited to, ELISA, competitive ELISA, BIAcore™ surface plasmon resonance analysis, in vitro and in vivo neutralization assays, and immunohistochemistry with tissue sections from different sources, including human, primate, or any other source as the need may be.

The term "inhibit" or "inhibiting" means neutralizing, antagonizing, prohibiting, preventing, restraining, slowing, disrupting, stopping, or reversing progression or severity of that which is being inhibited, including, but not limited to, a biological activity or property, or a disease or condition. The term "neutralizing" or "antagonizing" in reference to an anti-human ghrelin (or anti-ghrelin) monoclonal antibody of the invention or the phrase "antibody that antagonizes (neutralizes) ghrelin activity" or "antagonizes (neutralizes) ghrelin" is intended to refer to an antibody whose binding to or contact with human ghrelin results in inhibition of a biological activity induced by acylated or des-acyl human ghrelin. Inhibition of human ghrelin biological activity can be assessed by measuring one or more in vitro or in vivo indicators of human ghrelin biological activity including, but not limited to, induction of weight loss, altered feeding, inhibition of receptor binding (see WO 01/87335 for exemplary receptor binding assay), or signal transduction in a ghrelin-receptor binding assay. Indicators of ghrelin biological activity can be assessed by one or more of the several in vitro or in vivo assays known in the art. For example, the ability of an anti-ghrelin antibody to neutralize or antagonize ghrelin activity is assessed by use of the FLIPR assay as described in Example 4 herein.

The terms "individual," "subject," and "patient" refer to a human.

The present invention encompasses humanized monoclonal antibodies, and antigen-binding portions thereof, that specifically bind both acylated human ghrelin and des-acyl human ghrelin. Such antibodies neutralize a human ghrelin or a human ghrelin biological activity, whether it be acylated human ghrelin or des-acyl human ghrelin, or both. The activity inhibited can be: (i) the binding of acylated human ghrelin to receptor GHS-R1a; (ii) signal transduction prompted by acylated human ghrelin binding GHS-R1a; (iii) binding of des-acyl human ghrelin to a binding partner with which it specifically binds; or (iv) signal transduction prompted by des-acyl human ghrelin binding a binding partner with which it specifically binds. Specific binding of the humanized monoclonal antibodies and antigen-binding portions thereof of the present invention to human ghrelin, both acylated and des-acyl forms, permits these molecules to be used as therapeutics or prophylactics for ghrelin-associated diseases and disorders, i.e., diseases or disorders that benefit from lowering or inhibiting a ghrelin bioactivity or the level of active ghrelin present in the subject.

In a preferred embodiment, the present invention provides isolated, humanized anti-human ghrelin monoclonal antibodies and antigen-binding portions thereof that bind both acylated and des-acyl human ghrelin. Such antibodies bind acylated human ghrelin with an equilibrium dissociation constant, $K_D$, in the range of from about 1730 pM to about 11 pM (as determined by solid phase BIAcore™ surface plasmon resonance at room temperature), and antagonize an activity of human ghrelin, such as acylated human ghrelin mediated increase in intracellular calcium in hamster AV12 cells stably transfected to express human ghrelin receptor GHS-R1a, with an $IC_{50}$ of about 10 nM or less.

The preferred human framework amino acid sequence for the light chain variable region of the antibodies of the present invention comprises the following sequence, which, for illustrative purposes, is represented with the CDRs of Fab 3a (bolded and underlined) disclosed herein:

(SEQ ID NO: 4)
DIVMTQSPLSLPVTPGEPASISCRSSDSLGHSSGFTYLSWYLQKPGQSPGLLIYKVSNRFDGVPDRF

SGSGSGTDFTLKISRVEAEDVGVYYCSQSTLVPWTFGQGTKLEIK

The preferred human framework amino acid sequence for the heavy chain variable region of the antibodies of the present invention comprises the following sequence, which, for illustrative purposes, is represented with the CDRs of Fab 3a (bolded and underlined) disclosed herein:

(SEQ ID NO: 5)
QVQLVQSGAEVKKPGASVKVSCKVSGYTFTSGWMHWVRQAPGKGLEWMGYIDPSTGYTEYT

QKFKDRVTMTEDTSTDTAYMELSSLRSEDTAVYYCATDGYDYDYWGQGTTVTVSS

Human constant domain sequences are well known in the art and have been reported in the literature. Preferred human constant light chain sequences include the kappa and lambda constant light chain sequences. Preferred human constant heavy chain sequences include human gamma 1, human gamma 2, human gamma 3, human gamma 4, and mutated versions thereof that provide for altered effect or function, for example enhanced in vivo half-life, reduced Fc receptor binding, and the like. Human gamma 1 and human gamma 4, as well as variants thereof known in the art, are particularly preferred.

In some instances, humanized antibodies produced by grafting non-human CDRs from an antibody that binds amino acids 14-27 of human ghrelin onto selected human frameworks will provide humanized antibodies having the desired affinity to human ghrelin. However, it may be necessary or desirable to further modify specific residues of the selected human framework, or one or more CDRs, in order to enhance antigen binding. Preferably, those framework residues of the parent antibody that maintain or affect combining-site structures will be retained. These residues can be identified by X-ray crystallography of the parent antibody or Fab fragment, thereby identifying the three-dimensional structure of the antigen-binding site.

The present invention further encompasses variants and equivalents substantially homologous to the humanized antibodies and antibody fragments disclosed herein containing one or two conservative amino acid substitution mutations within the CDRs that do not adversely affect affinity or specificity. Such variants and equivalents can also contain a deletion of a terminal amino acid of a CDR.

Diagnostic Uses

Humanized antibodies of the present invention can be used to diagnose a disease or disorder associated with the expression of human ghrelin, either in acylated or des-acyl form, or to monitor ghrelin levels in a subject being treated, or being considered for treatment, for a ghrelin-associated condition. Diagnostic assays include methods that utilize antibodies of the present invention and a label to detect acylated ghrelin and/or des-acyl ghrelin in a sample such as a human body fluid, or in a cell or tissue extract, and include, for example, protocols such as ELISAs, RIAs, and FACS.

Therapeutic Uses

Pharmaceutical compositions comprising monoclonal antibodies of the present invention may be used to treat or prevent obesity and/or obesity-related disorders such as non-insulin dependent diabetes mellitus (NIDDM; Type II diabetes), Prader-Willi syndrome, impaired satiety, hyperphagia, anxiety, gastric motility disorders (including e.g., irritable bowel syndrome and functional dyspepsia), insulin resistance syndrome, metabolic syndrome, dyslipidemia, atherosclerosis, hypertension, hyperandrogenism, polycystic ovarian syndrome, cardiovascular disorders, and various cancers, such as liver cancer, prostate cancer, heart cancer, pancreatic cancer, adrenal cancer, pituitary cancer, bone cancer, and breast cancer. Such antibodies may also be used to treat or prevent eating disorders including, but not limited to, bulimia, anorexia nervosa, and binge eating.

The use of an anti-human ghrelin monoclonal antibody of the present invention as a medicament for treating or preventing at least one of the aforementioned disorders in which ghrelin (acylated or desacyl, or both) activity is detrimental is also contemplated herein. Additionally, the use of an anti-ghrelin monoclonal antibody of the present invention in the manufacture of a medicament for the treatment of at least one of the aforementioned disorders in which ghrelin activity is detrimental is also contemplated.

As used herein, the terms "treatment", "treating", and the like, refer to obtaining a desired pharmacologic and/or physiologic effect. The term "treatment" includes administration of a compound of the present invention to a mammal, particularly a human, for the purpose of inhibiting the disease, i.e., arresting its development or relieving the disease, i.e., causing regression of the disease or disorder, or alleviating symptoms or complications thereof. The effect may be a partial or complete cure for a disease and/or adverse affect attributable to the disease. Treatment may be in conjunction with behavior modification such as limitation of food intake and exercise. Treating obesity therefore includes inhibition of food intake, inhibition of weight gain, and/or inducing weight loss in subjects in need thereof. The therapeutic effect may also be prophylactic, i.e., completely or partially preventing a disease or symptom from occurring in a subject who may be predisposed to the disease, but who has not yet been diagnosed as having it.

Dosage regimens may be adjusted to provide the optimum desired response (e.g. a therapeutic or prophylactic response). For example, a single bolus may be administered, several divided doses may be administered over time, or the dose may be proportionally reduced or increased as indicated by the exigencies of the therapeutic situation.

Pharmaceutical Compositions

Humanized antibodies and antigen-binding portions thereof of the present invention can be incorporated into pharmaceutical compositions suitable for administration to a subject. Such antibody compounds can be administered alone, or in combination with a pharmaceutically acceptable carrier, diluent, or excipient, in single or multiple doses. Pharmaceutical compositions can also comprise combinations of antibodies disclosed herein. Such pharmaceutical compositions are designed to be appropriate for the selected mode or route of administration, and pharmaceutically acceptable diluents, carriers, and/or excipients such as dispersing agents, buffers, surfactants, preservatives, solubilizing agents, isotonicity agents, stabilizing agents, and the like are used as appropriate. Such compositions can be designed in accordance with conventional techniques as disclosed, for example, in Remington, *The Science and Practice of Pharmacy*, 19$^{th}$ Edition, Gennaro, Ed., Mack Publishing Co., Easton, Pa. 1995. Suitable carriers for pharmaceutical compositions include any material which, when combined with a monoclonal antibody of the present invention, retains the molecule's activity and is non-reactive with the subject's immune system.

Pharmaceutical compositions comprising anti-human ghrelin monoclonal antibodies of the present invention can be administered to a subject at risk for, or exhibiting, pathologies associated with obesity or related disorders, or various cancers, as described herein using standard administration techniques including oral, parenteral, via inhalation, or topical, including intravenous, intraperitoneal, subcutaneous, pulmonary, transdermal, intramuscular, intranasal, buccal, sublingual, or suppository administration (rectal or vaginal). Peripheral systemic delivery by intravenous, intraperitoneal, or subcutaneous injection is preferred.

Such pharmaceutical compositions preferably contain an "effective amount" or "therapeutically effective amount," or a "prophylactically effective amount," of one or more antibodies of the invention. An "effective amount" or a "therapeutically effective amount" refers to an amount effective, at dosages and for periods of time necessary, to achieve the desired therapeutic result. An effective amount or a therapeutically effective amount of an antibody can vary according to factors such as the disease state, age, sex, and weight of the individual, and the ability of the antibody or antibody portion to elicit a desired response in the individual. An effective amount or therapeutically effective amount is also one in which any toxic or detrimental effects of the antibody are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, a prophylactically effective amount will be less than a therapeutically effective amount.

An effective amount or a therapeutically effective amount is at least the minimal dose, but less than a toxic dose, of an active agent which is necessary to impart therapeutic benefit to a subject. Stated another way, such an amount for treating obesity, for example, is an amount that induces, ameliorates, or otherwise causes an improvement in the obese state of the mammal, for example by decreasing body mass index (BMI).

As is well known in the medical arts, dosages for any one subject depend on many factors, including the patient's size, body surface area, age, the particular compound to be administered, sex, time and route of administration, general health, and other drugs being administered concurrently. A typical dose for an antibody or antigen-binding portion thereof of the present invention can be, for example, in the range of from about 0.001 to about 1000 µg; however, doses below or above this exemplary range are envisioned, especially considering the aforementioned factors. The daily parenteral dosage regimen is about 0.1 µg/kg to about 100 mg/kg of total body weight, preferably from about 0.3 µg/kg to about 10 mg/kg, more preferably from about 1 µg/kg to 1 mg/kg, and even more preferably from about 0.5 to 10 mg/kg body weight per day. Patient progress can be monitored by periodic assessment, and the dose adjusted accordingly.

The following examples are offered for illustrative purposes only, and are not intended to limit the scope of the present invention in any way.

EXAMPLE 1

Humanization of Murine D4 Fab 3281

PCT International Publication No. WO 2006/019577 (PCT/US2005/023968) discloses the Fab portions of several murine monoclonal antibodies to the C-terminal end of human ghrelin, designated therein as Fabs 3281, 4731, and 4281. These Fabs bind both the acylated and unacylated forms of human ghrelin at an antigenic epitope located within amino acids 14-27 of this peptide. The affinity ($K_D$) of these Fabs for full length (1-28), C8-acylated human ghrelin is in the range from $4.36 \times 10^{-9}$ to $8.62 \times 10^{-11}$ M (4360 pM to 86.2 pM).

The amino acid sequences of the light chain and heavy chain variable regions of murine D4 Fab 3281 are shown below, with the CDR regions bolded and underlined:

Murine D4 Fab 3281

```
Light Chain
                                                          (SEQ ID NO: 2)
STPAWADAVMTQIPLTLSVTIGQPASISCRSSQSLGHSNGNTYLHWYLQKPGQSPKLLIY
KVSNRFSGVPDRFSGSGSGTDFTLKISRVEAEDLGTYFCSQSTLVPWTFGGGTKLEIKRA
DAAPTV Heavy Chain
                                                          (SEQ ID NO: 3)
QVQLQQSRAELAKPGASVKMSCKASGYTFTSYWMHWVKQGPGQGLEWIGYINPSTGYTEYTQ
KFKDKATLTADKSSSTAYMQLSSLTSEDSAVYYCATDGYDEDYWGQGTTLTVSSAKTTPP
```

Introduction of amino acid changes into CDRs of both the light and heavy chain variable regions of murine D4 Fab 3281 is performed by modifying appropriate codons in the encoding DNAs via conventional molecular biological techniques. The amino acid sequences of the CDRS in humanized Fabs of the present invention are shown in Table 1.

TABLE 1

| CDR Amino Acid Sequences of Humanized D4 Fabs | | | |
|---|---|---|---|
| Light Chain | CDR1 | CDR2 | CDR3 |
| D4 7.1* LCVR | RSSDSLGHSNGNTYLS (SEQ ID NO: 6) | KVSNRFD (SEQ ID NO: 17) | SQSTLVPWT (SEQ ID NO: 20) |
| 3a LCVR | RSSDSLGHSSGFTYLS (SEQ ID NO: 7) | KVSNRFD (SEQ ID NO: 17) | SQSTLVPWT (SEQ ID NO: 20) |
| 5a LCVR | RSSDHLGHSSGFTYLS (SEQ ID NO: 8) | KVSNRFD (SEQ ID NO: 17) | SQSTLVPWT (SEQ ID NO: 20) |
| 9a LCVR | RSSDSLGHSSGFTYLS (SEQ ID NO: 7) | KVSNRFD (SEQ ID NO: 17) | SQSTLVPWT (SEQ ID NO: 20) |
| A2 LCVR | RSSDSLGHSTGFTYLS (SEQ ID NO: 9) | KVSNRFD (SEQ ID NO: 17) | SQSTLVPWT (SEQ ID NO: 20) |
| A4 LCVR | RSSDSLGHSTGFTYLS (SEQ ID NO: 9) | KVSNRFD (SEQ ID NO: 17) | SQSTLVPWT (SEQ ID NO: 20) |
| A5 LCVR | RSSDHLGHSTGYTYLS (SEQ ID NO: 10) | KVSNRFD (SEQ ID NO: 17) | SQSTLVPWT (SEQ ID NO: 20) |
| 1b1 LCVR | RSSDSLGHSSGHTYLS (SEQ ID NO: 11) | KVSNRFD (SEQ ID NO: 17) | SQSTLVPWT (SEQ ID NO: 20) |
| D27Q LCVR | RSSQSLGHSSGHTYLS (SEQ ID NO: 12) | KVSNRFD (SEQ ID NO: 17) | SQSTLVPWT (SEQ ID NO: 20) |
| D52N LCVR | RSSDSLGHSSGHTYLS (SEQ ID NO: 11) | KVSNRFD (SEQ ID NO: 17) | SQSTLVPWT (SEQ ID NO: 20) |

TABLE 1-continued

CDR Amino Acid Sequences of Humanized D4 Fabs

| | CDR1 | CDR2 | CDR3 |
|---|---|---|---|
| D56S LCVR | RSSDSLGHSSGHTYLS (SEQ ID NO: 11) | KVSNRFS (SEQ ID NO: 18) | SQSTLVPWT (SEQ ID NO: 20) |
| S34H LCVR | RSSDSLGHSSGHTYLH (SEQ ID NO: 13) | KVSNRFD (SEQ ID NO: 17) | SQSTLVPWT (SEQ ID NO: 20) |
| T32Y LCVR | RSSDSLGHSSGHTYLS (SEQ ID NO: 11) | KVSNRFD (SEQ ID NO: 17) | SQSTLVPWT (SEQ ID NO: 20) |
| S28D LCVR | RSSDSLGHSDGNTYLS (SEQ ID NO: 14) | KVSNRFD (SEQ ID NO: 17) | SQSTLVPWT (SEQ ID NO: 20) |
| H30N LCVR | RSSDSLGHSSGNTYLS (SEQ ID NO: 15) | KVSNRFD (SEQ ID NO: 17) | SQSTLVPWT (SEQ ID NO: 20) |
| Consensus LCVR | RSSX$_1$X$_2$LGHSX$_3$GX$_4$TYLX$_5$ (SEQ ID NO: 16) | KVSNRFX$_6$ (SEQ ID NO: 19) | SQSTLYPWT (SEQ ID NO: 20) |

| Heavy Chain | CDR1 | CDR2 | CDR3 |
|---|---|---|---|
| D4 7.1* HCVR | GYTFTSTWMH (SEQ ID NO: 21) | YIDPSTGYTEYTQKFKD (SEQ ID NO: 25) | DGYDYDY (SEQ ID NO: 28) |
| 3a HCVR | GYTFTSGWMH (SEQ ID NO: 22) | YIDPSTGYTEYTQKFKD (SEQ ID NO: 25) | DGYDYDY (SEQ ID NO: 28) |
| 5a HCVR | GYTFTSTWMH (SEQ ID NO: 22) | YIDPSTGYTEYTQKFKD (SEQ ID NO: 25) | DGYDYDY (SEQ ID NO: 28) |
| 9a HCVR | GYTFTSTWMH (SEQ ID NO: 22) | YIDPSTGYTEYTQKFKD (SEQ ID NO: 25) | DGYDYDY (SEQ ID NO: 28) |
| A2 HCVR | GYTFTSTWMH (SEQ ID NO: 22) | YIDPSTGYTEYTQKFKD (SEQ ID NO: 25) | DGYDFDY (SEQ ID NO: 29) |
| A4 HCVR | GYTFTSTWMH (SEQ ID NO: 22) | YIDPSTGYTEYTQKFKD (SEQ ID NO: 25) | DGYDFDY (SEQ ID NO: 29) |
| A5 HCVR | GYTFTSTWMH (SEQ ID NO: 22) | YIDPSTGYTEYTQKFKD (SEQ ID NO: 25) | DGYDYDY (SEQ ID NO: 28) |
| 1b1 HCVR | GYTFTSTWMH (SEQ ID NO: 22) | YIDPSTGYTEYTQKFKD (SEQ ID NO: 25) | DGYDEDY (SEQ ID NO: 30) |
| D27Q HCVR | GYTFTSTWMH (SEQ ID NO: 22) | YIDPSTGYTEYTQKFKD (SEQ ID NO: 25) | DGYDEDY (SEQ ID NO: 30) |
| D52N HCVR | GYTFTSTWMH (SEQ ID NO: 22) | YINPSTGYTEYTQKFKD (SEQ ID NO: 26) | DGYDEDY (SEQ ID NO: 30) |
| D56S HCVR | GYTFTSTWMH (SEQ ID NO: 22) | YIDPSTGYTEYTQKFKD (SEQ ID NO: 25) | DGYDEDY (SEQ ID NO: 30) |
| S34H HCVR | GYTFTSTWMH (SEQ ID NO: 22) | YIDPSTGYTEYTQKFKD (SEQ ID NO: 25) | DGYDEDY (SEQ ID NO: 30) |
| T32Y HCYR | GYTFTSYWMH (SEQ ID NO: 23) | YIDPSTGYTEYTQKFKD (SEQ ID NO: 25) | DGYDEDY (SEQ ID NO: 30) |
| S28D HCVR | GYTFTSTWMH (SEQ ID NO: 22) | YIDPSTGYTEYTQKFKD (SEQ ID NO: 25) | DGYDEDY (SEQ ID NO: 30) |
| H30N HCVR | GYTFTSTWMH (SEQ ID NO: 22) | YIDPSTGYTEYTQKFKD (SEQ ID NO: 25) | DGYDEDY (SEQ ID NO: 30) |

TABLE 1-continued

CDR Amino Acid Sequences of Humanized D4 Fabs

| Consensus HCVR | GYTFTSX$_7$WMH (SEQ ID NO: 24) | YIX$_8$PSTGYTEYTQKFKD (SEQ ID NO: 27) | DGYDX$_9$DY (SEQ ID NO: 31) |

$^+$D4 7.1 LCVR and HCVR CDRs are mouse-optimized sequences in appropriate murine LCVR and HCVR frameworks, respectively.
As used throughout Table 1:
X$_1$ is Q or D;
X$_2$ is S or H;
X$_3$ is N, S, T, or D;
X$_4$ is N, F, Y, or H;
X$_5$ is H or S;
X$_6$ is S or D;
X$_7$ is Y, T, or G;
X$_8$ is N or D;
X$_9$ is E, Y, or F Entire light chain and heavy chain variable regions are produced by incorporating appropriate CDRs into human light chain and heavy chain framework amino acid sequences.

The preferred human framework amino acid sequence for the light chain variable region of the antibodies of the present invention comprises the following sequence, which for illustrative purposes is represented with the CDRs of Fab 3a (bolded and underlined) disclosed herein:

(SEQ ID NO: 4)
DIVMTQSPLSLPVTPGEPASISCRSSDSLGHSSGFTYLSWYLQKPGQSPGLLIYKVSNRFDGVPDRF

SGSGSGTDFTLKISRVEAEDVGVYYCSQSTLVPWTFGQGTKLEIK

The preferred human framework amino acid sequence for the heavy chain variable region of the antibodies of the present invention comprises the following sequence, which for illustrative purposes is represented with the CDRs of Fab 3a (bolded and underlined) disclosed herein:

(SEQ ID NO: 5)
QVQLVQSGAEVKKPGASVKVSCKVSGYTFTSGWMHWVRQAPGKGLEWMGYIDPSTGYTEYT

QKFKDRVTMTEDTSTDTAYMELSSLRSEDTAVYYCATDGYDYDYWGQGTTVTVSS

Table 2 shows the light chain variable region alignment of the present Fabs.

TABLE 2

Fab Light Chain Variable Region Alignment

| Fab | CDR1 |
|---|---|
| 3a | DIVMTQSPLS LPVTPGEPAS ISCRSSDSLG HSSGFTYLSW |
| 5a | DIVMTQSPLS LPVTPGEPAS ISCRSSDHLG HSSGFTVLSW |
| 9a | DIVMTQSPLS LPVTPGEPAS ISCRSSDSLG HSSGFTYLSW |
| A2 | DIVMTQSPLS LPVTPGEPAS ISCRSSDSLG HSTGFTYLSW |
| A4 | DIVMTQSPLS LPVTPGEPAS ISCRSSDSLG HSTGFTYLSW |
| A5 | DIVMTQSPLS LPVTPGEPAS ISCRSSDSLG HSTGYTYLSW |
| 1b1 | DIVMTQSPLS LPVTPGEPAS ISCRSSDSLG HSSGHTVLSW |
| D27Q | DIVMTQSPLS LPVTPGEPAS ISCRSSDSLG HSSGHTYLSW |
| D52N | DIVMTQSPLS LPVTPGEPAS ISCRSSDSLG HSSGHTYLSW |
| D56S | DIVMTQSPLS LPVTPGEPAS ISCRSSDSLG HSSGHTYLSW |
| S34H | DIVMTQSPLS LPVTPGEPAS ISCRSSDSLG HSSGHTYLHW |
| T32Y | DIVMTQSPLS LPVTPGEPAS ISCRSSDSLG HSSGHTYLSW |
| S28D | DIVMTQSPLS LPVTPGEPAS ISCRSSDSLG HSSGNTYLSW |
| H30N | DIVMTQSPLS LPVTPGEPAS ISCRSSDSLG HSSGNTVLSW |

TABLE 2-continued

Fab Light Chain Variable Region Alignment

| Fab | CDR2 |
|---|---|
| 3a | YLQKPGQSPG LLIYKVSNRF DGVPDRFSGS GSGTDFTLKI |
| 5a | YLQKPGQSPG LLIYKVSNRF DGVPDRFSGS GSGTDFTLKI |
| 9a | YLQKPGQSPG LLIYKVSNRF DGVPDRFSGS GSGTDFTLKI |
| A2 | YLQKPGQSPG LLIYKVSNRF DGVPDRFSGS GSGTDFTLKI |
| A4 | YLQKPGQSPG LLIYKVSNRF DGVPDRFSGS GSGTDFTLKI |
| A5 | YLQKPGQSPG LLIYKVSNRF DGVPDRFSGS GSGTDFTLKI |
| 1b1 | YLQKPGQSPG LLIYKVSNRF DGVPDRFSGS GSGTDFTLKI |
| D27Q | YLQKPGQSPG LLIYKVSNRF DGVPDRFSGS GSGTDFTLKI |
| D52N | YLQKPGQSPG LLIYKVSNRF DGVPDRFSGS GSGTDFTLKI |
| D56S | YLQKPGQSPG LLIYKVSNRF SGVPDRFSGS GSGTDFTLKI |
| S34H | YLQKPGQSPG LLIYKVSNRF DGVPDRFSGS GSGTDFTLKI |
| T32Y | YLQKPGQSPG LLIYKVSNRF DGVPDRFSGS GSGTDFTLKI |
| S28D | YLQKPGQSPG LLIYKVSNRF DGVPDRFSGS GSGTDFTLKI |
| H30N | YLQKPGQSPG LLIYKVSNRF DGVPDRFSGS GSGTDFTLKI |

| | CDR3 | |
|---|---|---|
| 3a | SRVEAEDVGV YYCSQSTLVP WTFGQGTKLE IK | (SEQ ID NO: 4) |
| 5a | SRVEAEDVGV YYCSQSTLVP WTFGQGTKLE IK | (SEQ ID NO: 32) |

TABLE 2-continued

Fab Light Chain Variable Region Alignment

| Fab | Sequence | |
|---|---|---|
| 9a | SRVEAEDVGV YYCSQSTLVP WTFGQGTKLE IK | (SEQ ID NO: 33) |
| A2 | SRVEAEDVGV YYCSQSTLVP WTFGQGTKLE IK | (SEQ ID NO: 34) |
| A4 | SRVEAEDVGV YYCSQSTLVP WTFGQGTKLE IK | (SEQ ID NO: 35) |
| A5 | SRVEAEDVGV YYCSQSTLVP WTFGQGTKLE IK | (SEQ ID NO: 36) |
| 1b1 | SRVEAEDVGV YYCSQSTLVP WTFGQGTKLE IK | (SEQ ID NO: 37) |
| D27Q | SRVEAEDVGV YYCSQSTLVP WTFGQGTKLE IK | (SEQ ID NO: 38) |
| D52N | SRVEAEDVGV YYCSQSTLVP WTFGQGTKLE IK | (SEQ ID NO: 39) |
| D56S | SRVEAEDVGV YYCSQSTLVP WTFGQGTKLE IK | (SEQ ID NO: 40) |
| S34H | SRVEAEDVGV YYCSQSTLVP WTFGQGTKLE IK | (SEQ ID NO: 41) |
| T32Y | SRVEAEDVGV YYCSQSTLVP WTFGQGTKLE IK | (SEQ ID NO: 42) |
| S28D | SRVEAEDVGV YYCSQSTLVP WTFGQGTKLE IK | (SEQ ID NO: 43) |
| H30N | SRVEAEDVGV YYCSQSTLVP WTFGQGTKLE IK | (SEQ ID NO: 44) |

Table 3 shows the heavy chain variable region alignment of the present Fabs.

TABLE 3

Fab Heavy Chain Variable Region Alignment

CDR1

| Fab | Sequence |
|---|---|
| 3a | QVQLVQSGAE VKKPGASVKV SCKVSGYTFT SGWMHWVRQA |
| 5a | QVQLVQSGAE VKKPGASVKV SCKVSGYTFT STWMHWVRQA |
| 9a | QVQLVQSGAE VKKPGASVKV SCKVSGYTFT STWMHWVRQA |
| A2 | QVQLVQSGAE VKKPGASVKV SCKVSGYTFT STWMHWVRQA |
| A4 | QVQLVQSGAE VKKPGASVKV SCKVSGYTFT STWMHWVRQA |
| A5 | QVQLVQSGAE VKKPGASVKV SCKVSGYTFT STWMHWVRQA |
| 1b1 | QVQLVQSGAE VKKPGASVKV SCKVSGYTFT STWMHWVRQA |
| D27Q | QVQLVQSGAE VKKPGASVKV SCKVSGVTFT STWMHWVRQA |
| D52N | QVQLVQSGAE VKKPGASVKV SCKVSGYTFT STWMHWVRQA |
| D56S | QVQLVQSGAE VKKPGASVKV SCKVSGYIFT STWMHWVRQA |
| S34H | QVQLVQSGAE VKKPGASVKV SCKVSGYTFT STWMHWVRQA |
| T32Y | QVQLVQSGAE VKXPGASVKV SCKVSGYTFT SYWMHWVRQA |
| S28D | QVQLVQSGAE VKKPGASVKV SCKVSGYTFT STWMHWVRQA |
| H30N | QVQLVQSGAE VKKPGASVKV SCKVSGYTFT STWMHWVRQA |

CDR2

| Fab | Sequence |
|---|---|
| 3a | PGKGLEWMGY IDPSTGYTEY TQKFKDRVTM TEDTSTDTAY |
| 5a | PGKGLEWMGY IDPSTGYTEY TQKFKDRVTM TEDTSTDTAY |
| 9a | PGKGLEWMGY IDPSTGYTEY TQKFKDRVTM TEDTSTDTAY |
| A2 | PGKGLEWMGY IDPSTGVTEY TQKFKDRVTM TEDTSTDTAY |
| A4 | PGKGLEWMGY IDPSTGYTEY TQKEKDRVTM TEDTSTDTAY |
| A5 | PGKGLEWMGY IDPSTGYTEY TQKFKDRVTM TEDTSTDTAY |
| 1b1 | PGKGLEWMGY IDPSTGVTEY TQKVKDRVTM TEDTSTDTAY |
| D27Q | PGKGLEWMGY IDPSTGYTEY TQKFKDRVTM TEDTSTDTAY |
| D52N | PGKGLEWMGY INPSTGYTEY TQKEKDRVTM TEDTSTDTAY |
| D56S | PGKGLEWMGY IDPSTGVTEY TQKFKDRVTM TEDTSTDTAY |
| S34H | PGKGLEWMGY IDPSTGVTEY TQKFKDRVTM TEDTSTDTAY |
| T32Y | PGKGLEWMGY IDPSTGVTEY TQKFKDRVTM TEDTSTDTAY |
| S28D | PGKGLEWMGY IDPSTGVTEY TQKFKDRVTM TEDTSTDTAY |
| H30N | PGKGLEWMGY IDPSTGVTEY TQKFKDRVTM TEDTSTDTAY |

CDR3

| Fab | Sequence | |
|---|---|---|
| 3a | MELSSLRSED TAVYYCATDG YDYDYWGQGT TVTVSS | (SEQ ID NO: 5) |
| 5a | MELSSLRSED TAVYYCATDG YDYDYWGQGT TVTVSS | (SEQ ID NO: 45) |
| 9a | MELSSLRSED TAVYYCATDG YDYDYWGQGT TVTVSS | (SEQ ID NO: 46) |
| A2 | MELSSLRSED TAVYYCATDG YDFDYWGQGT TVTVSS | (SEQ ID NO: 47) |
| A4 | MELSSLRSED TAVYYCATDG YDFDYWGQGT TVTVSS | (SEQ ID NO: 48) |
| A5 | MELSSLRSED TAVYYCATDG YDYDYWGQGT TVTVSS | (SEQ ID NO: 49) |
| 1b1 | MELSSLRSED TAVYYCATDG YDEDYWGQGT TVTVSS | (SEQ ID NO: 50) |
| D27Q | MELSSLRSED TAVYYCATDG YDEDYWGQGT TVTVSS | (SEQ ID NO: 51) |
| D52N | MELSSLRSED TAVYYCATDG YDEDYWGQGT TVTVSS | (SEQ ID NO: 52) |
| D56S | MELSSLRSED TAVYYCATDG YDEDYWGQGT TVTVSS | (SEQ ID NO: 53) |
| S34H | MELSSLRSED TAVYYCATDG YDEDYWGQGT TVTVSS | (SEQ ID NO: 54) |
| T32Y | MELSSLRSED TAVYYCATDG YDEDYWGQGT TVTVSS | (SEQ ID NO: 55) |
| S28D | MELSSLRSED TAVYYCATDG YDEDYWGQGT TVTVSS | (SEQ ID NO: 56) |
| H30N | MELSSLRSED TAVYYCATDG YDEDYWGQGT TVTVSS | (SEQ ID NO: 57) |

The sequences of the LCVR and HCVR of mouse-optimized Fab D4 7.1, with the CDRs bolded and underlined, are as follows:

```
Fab D4 7.1 LCVR
                                                   (SEQ ID NO: 58)
DAVMTQIPLTLSVTIGQPASISCRSSDSLGHSNGNTYLSWYLQKPGQSPK
LLIYKVSNRFDGVPDRFSGSGSGTDFTLKISRVEAEDLGTYFCSQSTLVP
WTFGGGTKLEIK

Fab D4 7.1 HCVR
                                                   (SEQ ID NO: 59)
QVQLQQSRAELAKPGASVKMSCKASGYTFTSTWMHWVKQGPGQGLEWIGY
IDPSTGYTEYTQKFKDKATLTADKSSSTAYMQLSSLTSEDSAVYYCATDG
YDYDYWGQGTTLTVSS
```

EXAMPLE 2

Affinity of Humanized D4 Fabs for Acylated Human Ghrelin

The affinity ($K_D$) of humanized/optimized anti-ghrelin Fabs disclosed in Example 1 for C-8 acylated human ghrelin (1-28) is measured using a BIAcore™ 2000 instrument containing a CM5 sensor chip. Except where noted, all reagents and materials are purchased from BIAcore™ AB (Uppsala, Sweden). Measurements are performed at about 25° C. Samples containing human ghrelin are dissolved in HBS-EP buffer (150 mM sodium chloride, 3 mM EDTA, 0.005% (w/v) surfactant P-20, and 10 mM HEPES, pH 7.4). A capture antibody, goat anti-mouse Kappa (Southern Biotechnology, Inc.) for the D4 and D4 7.1 Fabs, and goat anti-human kappa (Jackson ImmunoResearch) for all other Fabs, hereafter termed "capture antibody," is immobilized onto flow cells using amine-coupling chemistry. Flow cells (1-4) are activated for 7 minutes with a 1:1 mixture of 0.1 M N-hydroxysuccinimide and 0.1 M 3-(N,N-dimethylamino)propyl-N-ethylcarbodiimide at a flow rate of 10 μl/min. Goat anti-mouse Kappa or goat anti-human kappa (30 μg/mL in 10 mM sodium acetate, pH 4.5) is manually injected over all 4 flow cells at a flow rate of 10 μl/min. The surface density is monitored and additional capture antibody is injected if needed to individual cells until all flow cells reach a surface density of 4500-5000 response units (RU). Surfaces are blocked with a 7 minute injection of 1 M ethanolamine-HCl, pH 8.5 (10 μl/min). To ensure complete removal of any noncovalently bound capture antibody, 15 μl of 10 mM glycine, pH 1.5, is injected twice. Running buffer used for kinetic experiments contains 10 mM HEPES, pH 7.4, 150 mM NaCl, 0.005% P20.

Collection of kinetic binding data is performed at maximum flow rate (100 μl/min) and a low surface density to minimize mass transport effects. Each analysis cycle consists of: (i) capture of 300-350 RU of Fabs (BioSite) by injection of 5-10 μl of 5 μg/ml solution over flow cell 2, 3 and 4 for different Fabs at a flow rate of 10 μl/min., (ii) 200 μl injection (2 min.) of human ghrelin (concentration range of 50 nM to 0.39 nM in 2-fold dilution increments) over all 4 flow cells with flow cell 1 as the reference flow cell, (iii) 20 min. dissociation (buffer flow), (iv) regeneration of capture antibody surface with a 15 seq injection of 10 mM glycine, pH 1.5, (v) a 30 sec blank injection of running buffer, and (vi) a 2 min. stabilization time before the start of the next cycle. Signal is monitored as flow cell 2 minus flow cell 1, flow cell 3 minus flow cell 1, and flow cell 4 minus flow cell 1. Samples and a buffer blank are injected in duplicate in a random order. Data are processed using BIAevaluation v3.1 software and data are fit to a 1:1 binding model in either BIAevaluation v3.1 or CLAMP global analysis software.

Humanized Fabs disclosed herein exhibit affinities for full length, C-8 acylated human ghrelin ranging from 1730 μM to 20 μM as determined by BIAcore® 2000 surface plasmon resonance. For example, Fab A2 exhibits a $K_D$ of 43 μM, while Fab T32Y exhibits a $K_D$ of 1000 pM. $k_{on}$ values for Fabs of the present invention range from $5 \times 10^6$ 1/Ms to $3.05 \times 10^7$ 1/Ms. For example, Fab A2 exhibits a $k_{on}$ value of $6.34 \times 10^6$ 1/Ms, while Fab S28D exhibits a $k_{on}$ value of $3 \times 10^7$ 1/Ms. $k_{off}$ values for Fabs of the present invention range from $1.88 \times 10^{-4}$ 1/s to $1.90 \times 10^{-2}$ 1/s. For example, Fab A2 exhibits a off value of $2.7 \times 10^{-4}$ 1/s, while Fab T32Y exhibits a $k_{off}$ value of $8.75 \times 10^{-3}$ 1/s. Finally, the present Fabs exhibit a $t_{1/2}$ in minutes ranging from 0.6 to 61. For example, Fab T32Y exhibits a $t_{1/2}$ of 1 minute, while Fab A2 exhibits a $t_{1/2}$ of 43 minutes.

EXAMPLE 3

Affinities of Humanized D4 Monoclonal Antibodies for Various Ghrelins

The affinity ($K_D$) of humanized D4 anti-ghrelin monoclonal antibodies for acylated human ghrelin is measured using a BIAcore® 2000 instrument containing a CM5 sensor chip.

The monoclonal antibodies comprise the light chain variable region and heavy chain variable region sequences of the Fabs fused to a rat light chain kappa constant domain and a rat IgG1 heavy chain constant domain, respectively.

The amino acid sequence of the rat light chain kappa constant domain employed is:

```
Rat light chain kappa constant domain
                                                   (SEQ ID NO: 60)
DAAPTVSIFPPSTEQLATGGASVVCLMNNFYPRDISVKWKIDGTERRDGV

LDSVTDQDSKDSTYSMSSTLSLSKADYESHNLYTCEVVHKTSSSPVVKSF

NRNEC
```

The amino acid sequence of the rat IgG1 heavy chain constant domain employed is:

```
Rat IgG1 heavy chain constant domain
                                      (SEQ ID NO: 61)
TTAPSVYPLAPGTALKSNSMVTLGCLVKGYFPEPVTVTWNSGALSSGVHT

FPAVLQSGLYTLTSSVTVPSSTWPSQTVTCNVAHPASSTKVDKKIVPRNC

GGDCKPCICTGSEVSSVFIFPPKPKDVLTITLTPKVTCVVVDISQDDPEV

HFSWFVDDVEVHTAQTRPPEEQFNSTFRSVSELPILHQDWLNGRTFRCKV

TSAAFPSPIEKTISKPEGRTQVPHVYTMSPTKEEMTQNEVSITCMVKGFY

PPDIYVEWQMNGQPQENYKNTPPTMDTDGSYFLYSKLNVKKEKWQQGNTF

TCSVLHEGLHNHHTEKSLSHSPGK
```

Except where noted, all reagents and materials are purchased from BIAcore® AB (Uppsala, Sweden). All measurements are performed at about 25° C. All samples containing human ghrelin (full length, C-8 acylated or des-acyl) and anti-ghrelin Mabs are diluted in HBS-EP buffer (150 mM sodium chloride, 3 mM EDTA, 0.005% (w/v) surfactant P-20, and 10 mM HEPES, pH 7.4). For all of the Mabs, the antibody is directly coupled to a CM5 chip using the amine-coupling chemistry described below, aiming for a surface density of between 800-1000 response units (RU). Flow cells (1-4) are activated for 7 minutes with a 1:1 mixture of 0.1 M N-hydroxysuccinimide and 0.1 M 3-(N,N-dimethylamino)propyl-N-ethylcarbodiimide at a flow rate of 10 μl/min. The Mab is diluted to 10 μg/mL in 10 mM sodium acetate, pH 4.5, and manually injected over all four flow cells at a flow rate of 10 μl/min. The surface density is monitored, and additional capture antibody is injected as needed to each individual cell until all flow cells reach a surface density of 800-1000 RU. Surfaces are blocked with a seven minute injection of 1 M ethanolamine-HCl, pH 8.5(10 μl/min). To ensure complete removal of any noncovalently bound capture antibody, 15 μl of 10 mM glycine, pH 1.5, are injected twice. Running buffer for kinetic experiments is HBS-EP buffer (150 mM sodium chloride, 3 mM EDTA, 0.005% (w/v) surfactant P-20, and 10 mM HEPES, pH 7.4).

Collection of kinetic binding data is performed at maximum flow rate (100 μl/min) and a low surface density to minimize mass transport effects. Each analysis cycle consists of: (i) 200 μl injection (2 min.) of ghrelin (concentration range of 50 nM to 0.39 nM in 2-fold dilution increments) over all four flow cells with flow cell 1 as the reference flow cell; (ii) 20 min. dissociation (buffer only flow); (iii) regeneration of chip surface with a 15 sec injection of 10 mM glycine, pH 1.5; and (iv) a 2 min. stabilization time before the start of the next cycle. The signal is monitored as flow cell 2 minus flow cell 1, flow cell 3 minus flow cell 1, and flow cell 4 minus flow cell 1. Samples and a buffer blank are injected in duplicate in a random order. Data are processed using BIAevaluation v.4.1 software and data are fit to a 1:1 binding model in either BIAevaluation v.4.1 or CLAMP global analysis software.

Humanized/affinity matured antibodies disclosed herein exhibit affinities for C-8-acylated human ghrelin ranging from 931 pM to 11 pM as determined by BIAcore® 2000 surface plasmon resonance. For example, Mab A4 exhibits a $K_D$ of 74 μM, while Mab S34H exhibits a $K_D$ of 400 pM. $k_{on}$ values for Mabs of the present invention range from $4.44 \times 10^6$ l/Ms to $4.89 \times 10^7$ 1/Ms. For example, Mab A4 exhibits a $k_{on}$ value of $4.44 \times 10^6$ l/Ms, while Mab S34H exhibits a $k_{on}$ value of $4.24 \times 10^7$ l/Ms. $k_{off}$ values for Mabs of the present invention range from $4.98 \times 10^{-5}$ l/s to $2.58 \times 10^{-2}$ l/s. For example, Mab A5 exhibits a $k_{off}$ value of $5.74 \times 10^{-5}$ 1/s, while Mab S34H exhibits a $k_{off}$ value of $1.69 \times 10^{-2}$ 1/s. Finally, the present Mabs exhibit a $t_{1/2}$ in minutes ranging from 0 to 232. For example, Mab S34H exhibits a $t_{1/2}$ of 1 minute, while Mab A5 exhibits a $t_{1/2}$ of 201 minutes. The $t_{1/2}$ is calculated from the following equation: $t_{1/2}$ (sec) (ln 0.5)/($k_{off}$ in $s^{-1}$). This value is converted to minutes by dividing by 60, and is considered to be a theoretical half-life of the antibody:antigen complex. These binding kinetics are not due to the addition of a constant region (mouse or rat) as suggested by the similarity in affinity between the presently improved Fabs and Mabs.

Monoclonal antibodies of the present invention exhibit affinities for human des-acyl ghrelin ranging from 1320 pM to 14.1 pM as determined by BIAcore® 2000 surface plasmon resonance. For example, Mab D52N exhibits a $K_D$ of 1050 μM for human des-acyl ghrelin, while Mab D27Q exhibits a $K_D$ of 176 pM. $k_{on}$ values for Mabs of the present invention for human des-acyl ghrelin range from $4.32 \times 10^6$ l/Ms to $7.21 \times 10^7$ l/Ms. For example, Mab A4 exhibits a $k_{on}$ value of $4.56 \times 10^6$ l/Ms, while Mab D52N exhibits a $k_{on}$ value of $3.26 \times 10^7$ l/Ms. $k_{off}$ values for Mabs of the present invention for human des-acyl ghrelin range from $2.57 \times 10^{-5}$ l/s to $9.53 \times 10^{-2}$ l/s. For example, Mab A5 exhibits a $k_{off}$ value of $6.67 \times 10^{-5}$ l/s, while Mab D52N exhibits a $k_{off}$ value of $3.43 \times 10^{-2}$ l/s.

EXAMPLE 4

Activity of Humanized D4 Mabs in the In Vitro FLIPR Assay

The in vitro FLIPR® Calcium Assay system (Molecular Devices) is used with hamster AV12 cells stably transfected to express GHS-R1a (the human ghrelin receptor). This assay evaluates changes in intracellular calcium as a means of detecting ghrelin/GHS-R1a binding and signaling in the presence or absence of a humanized Mab of the present invention.

Transfected AV12 cells are grown in growth medium (DMEM/F12 (3:1), 5% fetal bovine serum, 50 μg/ml hygromycin, and 50 μg/ml zeocin) to about $50-90 \times 10^6$ cells per T-150 flask. The cells are then trypsinized, washed, and distributed into Biocoat black poly-D-lysine coated plates (60,000 cells in 100 μl growth medium per well). The cells are incubated for about 20 hours at 37° C. in 5% $CO_2$. The medium is removed from the plate and 150 μl HBSS (Gibco 14025-037) are added to each well, and then removed. Dye is then loaded into the cells by adding to each well 50 μl loading buffer (5 μM Fluo-4AM (Molecular Devices), 0.05% Pluronic in FLIPR buffer [Hank's Balanced Salt with calcium (HBSS, Gibco 14025-092) and 0.75% BSA (Gibco)]. The plate is further incubated at 37° C. in 5% $CO_2$ for one hour. The wells are then washed twice with HBSS and 50 μl FLIPR buffer are then added per well.

Samples are prepared by combining 7.2 μl calcium concentrate ($CaCl_2$-$2H_2O$ in water at 3.7 mg/ml mixed 1:1 with HBSS and filter sterilized), 30 μl Mab as disclosed in Example 3 (of varying concentration), and 16.8 µl of C-8 acylated, 1-28 human ghrelin (2.5 µM stock) in 3.75% BSA/50% HBSS. The final concentration of the sample solution is 0.75% BSA, and calcium at approximately the same concentration as in the FLIPR buffer. Fifty µl of the sample solution are added to the 50 µl FLIPR buffer in the well with the AV12 cells. The final concentration of the human ghrelin is 0.83 nM. The cell plate is shaken for about 15 seconds prior to loading it into the FLIPR instrument. Test samples or control samples are added to each well, and read by a Fluorometric Imaging Plate Reader (Molecular Devices).

If there is no Mab or an irrelevant antibody present in the solution, the acylated, full-length human ghrelin will be free to bind the GHS-R1a receptor on the AV12 cells, and signal transduction will occur, resulting in comparatively high values in the assay. If a Mab is present that binds to the full-length human ghrelin in the solution, then the binding of the full-length human ghrelin to the GHS-R1a receptor is inhibited, and signal transduction is inhibited, resulting in comparatively lower values in the assay. The Mab concentration used is determined by titration to be a level that will give approximately 95% inhibition of 1 nM human ghrelin activity.

Mabs disclosed herein exhibit $IC_{50}$ values in the range from 0.55 nM to 6.49 nM. For example, Mab D27Q exhibits an $IC_{50}$ value of 1.12 nM, while Mab S34N exhibits an $IC_{50}$ value of 2.55 nM.

EXAMPLE 5

Effect of a Chimeric Murine D4 Ghrelin Antibody on Body Weight in Diet-Induced Obese Male Rats This study is designed to determine the effect of administration of a D4 type antibody on body weight loss in diet-induced obese (DIO) rats.

Diet-induced obese (DIO) male Long-Evans rats (Harlan; Va.) maintained on a calorie rich diet (TD95217, Teklad, Madison, Wis.) since weaning are used. DIO is established by ad libitum feeding of a diet consisting of 40% fat, 39% carbohydrate, and 21% protein caloric content (TD95217) for at least 7 weeks. Animals are individually housed in a temperature-controlled (24° C.) facility with 12 hour light/dark cycle (lights on 2200) and free access to food (TD95217) and water. After 2 weeks acclimation to the facility, animals are randomized to study groups by body weight.

Body composition is measured by QNMR one day prior to the start of treatment and at the conclusion of treatment. Control isotype or chimeric murine D4 anti-ghrelin antibody (10 or 30 mg/kg) are administered subcutaneously every week on Days 0, 7, and 14. Daily food intake and body weights of the animals are monitored every morning before dark cycle of photoperiod for 21 days.

The chimeric murine D4 anti-ghrelin antibody comprises murine D4 Fab 3281 light and heavy chain variable regions, SEQ ID NOs:2 and 3, respectively, fused to a rat light chain kappa constant domain and a rat IgG1 heavy chain constant domain, SEQ ID NOs:60 and 61, respectively, as described above in Example 3.

Administration of the mouse/rat chimeric murine D4 ghrelin antibody results in a significant dose-response decrease in cumulative food intake, cumulative body weight change, and fat mass loss, respectively, in diet-induced obese male Long-Evans rats after 21 days treatment.

These results suggest that in this rat model of obesity, a D4 type anti-ghrelin antibody is effective in reducing food intake and obesity-related physiological parameters.

We claim:

1. A humanized monoclonal antibody or antigen-binding portion thereof, which binds human ghrelin, wherein:
   - each light chain variable region comprises the amino acid sequence shown in SEQ ID NO:4 and each heavy chain variable region comprises the amino acid sequence shown in SEQ ID NO:5;
   - each light chain variable region comprises the amino acid sequence shown in SEQ ID NO:32 and each heavy chain variable region comprises the amino acid sequence shown in SEQ ID NO:45;
   - each light chain variable region comprises the amino acid sequence shown in SEQ ID NO:33 and each heavy chain variable region comprises the amino acid sequence shown in SEQ ID NO:46;
   - each light chain variable region comprises the amino acid sequence shown in SEQ ID NO:34 and each heavy chain variable region comprises the amino acid sequence shown in SEQ ID NO:47;
   - each light chain variable region comprises the amino acid sequence shown in SEQ ID NO:35 and each heavy chain variable region comprises the amino acid sequence shown in SEQ ID NO:48;
   - each light chain variable region comprises the amino acid sequence shown in SEQ ID NO:36 and each heavy chain variable region comprises the amino acid sequence shown in SEQ ID NO:49;
   - each light chain variable region comprises the amino acid sequence shown in SEQ ID NO:37 and each heavy chain variable region comprises the amino acid sequence shown in SEQ ID NO:50;
   - each light chain variable region comprises the amino acid sequence shown in SEQ ID NO:38 and each heavy chain variable region comprises the amino acid sequence shown in SEQ ID NO:51;
   - each light chain variable region comprises the amino acid sequence shown in SEQ ID NO:39 and each heavy chain variable region comprises the amino acid sequence shown in SEQ ID NO:52;

each light chain variable region comprises the amino acid sequence shown in SEQ ID NO:40 and each heavy chain variable region comprises the amino acid sequence shown in SEQ ID NO:53;

each light chain variable region comprises the amino acid sequence shown in SEQ ID NO:41 and each heavy chain variable region comprises the amino acid sequence shown in SEQ ID NO:54;

each light chain variable region comprises the amino acid sequence shown in SEQ ID NO:42 and each heavy chain variable region comprises the amino acid sequence shown in SEQ ID NO:55;

each light chain variable region comprises the amino acid sequence shown in SEQ ID NO:43 and each heavy chain variable region comprises the amino acid sequence shown in SEQ ID NO:56; or each light chain variable region comprises the amino acid sequence shown in SEQ ID NO:44 and each heavy chain variable region comprises the amino acid sequence shown in SEQ ID NO:57.

2. A pharmaceutical composition, comprising said humanized monoclonal antibody or antigen-binding portion thereof of claim 1, and a pharmaceutically acceptable carrier, diluent, or excipient.

3. A method of neutralizing or inhibiting ghrelin activity, or decreasing active ghrelin levels, in a human, comprising administering to a human in need thereof an effective amount of said humanized monoclonal antibody or antigen-binding portion thereof of claim 1.

4. A method of treating a disease or disorder selected from the group consisting of obesity, non-insulin dependent diabetes mellitus, Prader-Willi syndrome, hyperphagia and impaired satiety, comprising administering to a patient in need thereof said humanized monoclonal antibody or antigen-binding thereof of claim 1.

\* \* \* \* \*

UNITED STATES PATENT AND TRADEMARK OFFICE
CERTIFICATE OF CORRECTION

| | |
|---|---|
| PATENT NO. | : 7,901,679 B2 |
| APPLICATION NO. | : 12/278419 |
| DATED | : March 8, 2011 |
| INVENTOR(S) | : David Matthew Marquis et al. |

It is certified that error appears in the above-identified patent and that said Letters Patent is hereby corrected as shown below:

On First Page, Column 2, Line 22, after "179" insert -- (1996). --

Signed and Sealed this
Twenty-sixth Day of April, 2011

David J. Kappos
*Director of the United States Patent and Trademark Office*

SEQUENCE LISTING

```
<160> NUMBER OF SEQ ID NOS: 61

<210> SEQ ID NO 1
<211> LENGTH: 28
<212> TYPE: PRT
<213> ORGANISM: Homo sapiens

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 126
<212> TYPE: PRT
<213> ORGANISM: Mus sp.

<400> SEQUENCE: 2

Ser Thr Pro Ala Trp Ala Asp Ala Val Met Thr Gln Ile Pro Leu Thr
1               5                   10                  15

Leu Ser Val Thr Ile Gly Gln Pro Ala Ser Ile Ser Cys Arg Ser Ser
            20                  25                  30

Gln Ser Leu Gly His Ser Asn Gly Asn Thr Tyr Leu His Trp Tyr Leu
        35                  40                  45

Gln Lys Pro Gly Gln Ser Pro Lys Leu Leu Ile Tyr Lys Val Ser Asn
    50                  55                  60
```

```
Arg Phe Ser Gly Val Pro Asp Arg Phe Ser Gly Ser Gly Ser Gly Thr
 65                  70                  75                  80

Asp Phe Thr Leu Lys Ile Ser Arg Val Glu Ala Glu Asp Leu Gly Thr
                 85                  90                  95

Tyr Phe Cys Ser Gln Ser Thr Leu Val Pro Trp Thr Phe Gly Gly Gly
            100                 105                 110

Thr Lys Leu Glu Ile Lys Arg Ala Asp Ala Ala Pro Thr Val
        115                 120                 125
```

<210> SEQ ID NO 3
<211> LENGTH: 122
<212> TYPE: PRT
<213> ORGANISM: Mus sp.

<400> SEQUENCE: 3

```
Gln Val Gln Leu Gln Gln Ser Arg Ala Glu Leu Ala Lys Pro Gly Ala
 1               5                  10                  15

Ser Val Lys Met Ser Cys Lys Ala Ser Gly Tyr Thr Phe Thr Ser Tyr
            20                  25                  30

Trp Met His Trp Val Lys Gln Gly Pro Gly Gln Gly Leu Glu Trp Ile
        35                  40                  45

Gly Tyr Ile Asn Pro Ser Thr Gly Tyr Thr Glu Tyr Thr Gln Lys Phe
 50                  55                  60

Lys Asp Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Thr Asp Gly Tyr Asp Glu Asp Tyr Trp Gly Gln Gly Thr Thr Leu
            100                 105                 110

Thr Val Ser Ser Ala Lys Thr Thr Pro Pro
        115                 120
```

<210> SEQ ID NO 4
<211> LENGTH: 112
<212> TYPE: PRT
<213> ORGANISM: Homo sapiens

<400> SEQUENCE: 4

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Asp Ser Leu Gly His Ser
            20                  25                  30

Ser Gly Phe Thr Tyr Leu Ser Trp Tyr Leu Gln Lys Pro Gly Gln Ser
        35                  40                  45

Pro Gly Leu Leu Ile Tyr Lys Val Ser Asn Arg Phe Asp Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr Leu Val Pro Trp Thr Phe Gly Gln Gly Thr Lys Leu Glu Ile Lys
            100                 105                 110
```

<210> SEQ ID NO 5
<211> LENGTH: 116
<212> TYPE: PRT
<213> ORGANISM: Homo sapiens

<400> SEQUENCE: 5

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Gly
            20                  25                  30

Trp Met His Trp Val Arg Gln Ala Pro Gly Lys Gly Leu Glu Trp Met
        35                  40                  45

Gly Tyr Ile Asp Pro Ser Thr Gly Tyr Thr Gly Tyr Thr Gln Lys Phe
    50                  55                  60

Lys Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Gly Tyr Asp Tyr Asp Tyr Trp Gly Gln Gly Thr Thr Val
            100                 105                 110

Thr Val Ser Ser
        115
```

<210> SEQ ID NO 6
<211> LENGTH: 16
<212> TYPE: PRT
<213> ORGANISM: Artificial
<220> FEATURE:
<223> OTHER INFORMATION: synthetic construct

<400> SEQUENCE: 6

```
Arg Ser Ser Asp Ser Leu Gly His Ser Asn Gly Asn Thr Tyr Leu Ser
1               5                   10                  15
```

<210> SEQ ID NO 7
<211> LENGTH: 16
<212> TYPE: PRT
<213> ORGANISM: Artificial
<220> FEATURE:
<223> OTHER INFORMATION: synthetic construct

<400> SEQUENCE: 7

```
Arg Ser Ser Asp Ser Leu Gly His Ser Ser Gly Phe Thr Tyr Leu Ser
1               5                   10                  15
```

<210> SEQ ID NO 8
<211> LENGTH: 16
<212> TYPE: PRT
<213> ORGANISM: Artificial
<220> FEATURE:
<223> OTHER INFORMATION: Synthetic construct

<400> SEQUENCE: 8

```
Arg Ser Ser Asp His Leu Gly His Ser Ser Gly Phe Thr Tyr Leu Ser
1               5                   10                  15
```

<210> SEQ ID NO 9
<211> LENGTH: 16
<212> TYPE: PRT
<213> ORGANISM: Artificial
<220> FEATURE:
<223> OTHER INFORMATION: synthetic construct

<400> SEQUENCE: 9

```
Arg Ser Ser Asp Ser Leu Gly His Ser Thr Gly Phe Thr Tyr Leu Ser
1               5                   10                  15
```

<210> SEQ ID NO 10
<211> LENGTH: 16

```
<212> TYPE: PRT
<213> ORGANISM: Artificial
<220> FEATURE:
<223> OTHER INFORMATION: synthetic construct

<400> SEQUENCE: 10

Arg Ser Ser Asp His Leu Gly His Ser Thr Gly Tyr Thr Tyr Leu Ser
1               5                   10                  15

<210> SEQ ID NO 11
<211> LENGTH: 16
<212> TYPE: PRT
<213> ORGANISM: Artificial
<220> FEATURE:
<223> OTHER INFORMATION: synthetic construct

<400> SEQUENCE: 11

Arg Ser Ser Asp Ser Leu Gly His Ser Gly His Thr Tyr Leu Ser
1               5                   10                  15

<210> SEQ ID NO 12
<211> LENGTH: 16
<212> TYPE: PRT
<213> ORGANISM: Artificial
<220> FEATURE:
<223> OTHER INFORMATION: synthetic construct

<400> SEQUENCE: 12

Arg Ser Ser Gln Ser Leu Gly His Ser Gly His Thr Tyr Leu Ser
1               5                   10                  15

<210> SEQ ID NO 13
<211> LENGTH: 16
<212> TYPE: PRT
<213> ORGANISM: Artificial
<220> FEATURE:
<223> OTHER INFORMATION: synthetic construct

<400> SEQUENCE: 13

Arg Ser Ser Asp Ser Leu Gly His Ser Gly His Thr Tyr Leu His
1               5                   10                  15

<210> SEQ ID NO 14
<211> LENGTH: 16
<212> TYPE: PRT
<213> ORGANISM: Artificial
<220> FEATURE:
<223> OTHER INFORMATION: synthetic construct

<400> SEQUENCE: 14

Arg Ser Ser Asp Ser Leu Gly His Ser Asp Gly Asn Thr Tyr Leu Ser
1               5                   10                  15

<210> SEQ ID NO 15
<211> LENGTH: 16
<212> TYPE: PRT
<213> ORGANISM: Artificial
<220> FEATURE:
<223> OTHER INFORMATION: synthetic construct

<400> SEQUENCE: 15

Arg Ser Ser Asp Ser Leu Gly His Ser Gly Asn Thr Tyr Leu Ser
1               5                   10                  15

<210> SEQ ID NO 16
<211> LENGTH: 16
<212> TYPE: PRT
<213> ORGANISM: Artificial
```

```
<220> FEATURE:
<223> OTHER INFORMATION: synthetic construct
<220> FEATURE:
<221> NAME/KEY: MISC_FEATURE
<222> LOCATION: (4)..(4)
<223> OTHER INFORMATION: Xaa at position 4 = Gln or Asp
<220> FEATURE:
<221> NAME/KEY: MISC_FEATURE
<222> LOCATION: (5)..(5)
<223> OTHER INFORMATION: Xaa at position 5 = Ser or His
<220> FEATURE:
<221> NAME/KEY: MISC_FEATURE
<222> LOCATION: (10)..(10)
<223> OTHER INFORMATION: Xaa at position 10 = Asn, Ser, Thr or Asp
<220> FEATURE:
<221> NAME/KEY: MISC_FEATURE
<222> LOCATION: (12)..(12)
<223> OTHER INFORMATION: Xaa at position 12 = Asn, Phe, Tyr, or His
<220> FEATURE:
<221> NAME/KEY: MISC_FEATURE
<222> LOCATION: (16)..(16)
<223> OTHER INFORMATION: Xaa at position 16 = His or Ser

<400> SEQUENCE: 16

Arg Ser Ser Xaa Xaa Leu Gly His Ser Xaa Gly Xaa Thr Tyr Leu Xaa
1               5                   10                  15

<210> SEQ ID NO 17
<211> LENGTH: 7
<212> TYPE: PRT
<213> ORGANISM: Artificial
<220> FEATURE:
<223> OTHER INFORMATION: synthetic construct

<400> SEQUENCE: 17

Lys Val Ser Asn Arg Phe Asp
1               5

<210> SEQ ID NO 18
<211> LENGTH: 7
<212> TYPE: PRT
<213> ORGANISM: Artificial
<220> FEATURE:
<223> OTHER INFORMATION: synthetic construct

<400> SEQUENCE: 18

Lys Val Ser Asn Arg Phe Ser
1               5

<210> SEQ ID NO 19
<211> LENGTH: 7
<212> TYPE: PRT
<213> ORGANISM: Artificial
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: Xaa at position 7 = Ser or Asp

<400> SEQUENCE: 19

Lys Val Ser Asn Arg Phe Xaa
1               5

<210> SEQ ID NO 20
<211> LENGTH: 9
<212> TYPE: PRT
<213> ORGANISM: Artificial
<220> FEATURE:
<223> OTHER INFORMATION: synthetic construct

<400> SEQUENCE: 20
```

```
Ser Gln Ser Thr Leu Val Pro Trp Thr
1               5

<210> SEQ ID NO 21
<211> LENGTH: 10
<212> TYPE: PRT
<213> ORGANISM: Artificial
<220> FEATURE:
<223> OTHER INFORMATION: synthetic construct

<400> SEQUENCE: 21

Gly Tyr Thr Phe Thr Ser Thr Trp Met His
1               5                   10

<210> SEQ ID NO 22
<211> LENGTH: 10
<212> TYPE: PRT
<213> ORGANISM: Artificial
<220> FEATURE:
<223> OTHER INFORMATION: synthetic construct

<400> SEQUENCE: 22

Gly Tyr Thr Phe Thr Ser Gly Trp Met His
1               5                   10

<210> SEQ ID NO 23
<211> LENGTH: 10
<212> TYPE: PRT
<213> ORGANISM: Artificial
<220> FEATURE:
<223> OTHER INFORMATION: synthetic construct

<400> SEQUENCE: 23

Gly Tyr Thr Phe Thr Ser Tyr Trp Met His
1               5                   10

<210> SEQ ID NO 24
<211> LENGTH: 10
<212> TYPE: PRT
<213> ORGANISM: Artificial
<220> FEATURE:
<223> OTHER INFORMATION: synthetic construct
<220> FEATURE:
<221> NAME/KEY: MISC_FEATURE
<222> LOCATION: (7)..(7)
<223> OTHER INFORMATION: Xaa at position 7 = Tyr, Thr or Gly

<400> SEQUENCE: 24

Gly Tyr Thr Phe Thr Ser Xaa Trp Met His
1               5                   10

<210> SEQ ID NO 25
<211> LENGTH: 17
<212> TYPE: PRT
<213> ORGANISM: Artificial
<220> FEATURE:
<223> OTHER INFORMATION: synthetic construct

<400> SEQUENCE: 25

Tyr Ile Asp Pro Ser Thr Gly Tyr Thr Glu Tyr Thr Gln Lys Phe Lys
1               5                   10                  15

Asp

<210> SEQ ID NO 26
<211> LENGTH: 17
<212> TYPE: PRT
<213> ORGANISM: Artificial
```

```
<220> FEATURE:
<223> OTHER INFORMATION: synthetic construct

<400> SEQUENCE: 26

Tyr Ile Asn Pro Ser Thr Gly Tyr Thr Glu Tyr Thr Gln Lys Phe Lys
1               5                   10                  15

Asp

<210> SEQ ID NO 27
<211> LENGTH: 17
<212> TYPE: PRT
<213> ORGANISM: Artificial
<220> FEATURE:
<223> OTHER INFORMATION: synthetic construct
<220> FEATURE:
<221> NAME/KEY: MISC_FEATURE
<222> LOCATION: (3)..(3)
<223> OTHER INFORMATION: Xaa at position 3 = Asn or Asp

<400> SEQUENCE: 27

Tyr Ile Xaa Pro Ser Thr Gly Tyr Thr Glu Tyr Thr Gln Lys Phe Lys
1               5                   10                  15

Asp

<210> SEQ ID NO 28
<211> LENGTH: 7
<212> TYPE: PRT
<213> ORGANISM: Artificial
<220> FEATURE:
<223> OTHER INFORMATION: synthetic construct

<400> SEQUENCE: 28

Asp Gly Tyr Asp Tyr Asp Tyr
1               5

<210> SEQ ID NO 29
<211> LENGTH: 7
<212> TYPE: PRT
<213> ORGANISM: Artificial
<220> FEATURE:
<223> OTHER INFORMATION: synthetic construct

<400> SEQUENCE: 29

Asp Gly Tyr Asp Phe Asp Tyr
1               5

<210> SEQ ID NO 30
<211> LENGTH: 7
<212> TYPE: PRT
<213> ORGANISM: Artificial
<220> FEATURE:
<223> OTHER INFORMATION: synthetic construct

<400> SEQUENCE: 30

Asp Gly Tyr Asp Glu Asp Tyr
1               5

<210> SEQ ID NO 31
<211> LENGTH: 7
<212> TYPE: PRT
<213> ORGANISM: Artificial
<220> FEATURE:
<223> OTHER INFORMATION: synthetic construct
<220> FEATURE:
<221> NAME/KEY: MISC_FEATURE
<222> LOCATION: (5)..(5)
<223> OTHER INFORMATION: Xaa at position 5 = Glu, Tyr, or Phe
```

```
<400> SEQUENCE: 31

Asp Gly Tyr Asp Xaa Asp Tyr
1               5

<210> SEQ ID NO 32
<211> LENGTH: 112
<212> TYPE: PRT
<213> ORGANISM: Artificial
<220> FEATURE:
<223> OTHER INFORMATION: synthetic construct

<400> SEQUENCE: 32

Asp Ile Val Met Thr Gln Ser Pro Leu Ser Leu Pro Val Thr Pro Gly
1               5                   10                  15

Glu Pro Ala Ser Ile Ser Cys Arg Ser Ser Asp His Leu Gly His Ser
            20                  25                  30

Ser Gly Phe Thr Tyr Leu Ser Trp Tyr Leu Gln Lys Pro Gly Gln Ser
        35                  40                  45

Pro Gly Leu Leu Ile Tyr Lys Val Ser Asn Arg Phe Asp Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Leu Val Pro Trp Thr Phe Gly Gln Gly Thr Lys Leu Glu Ile Lys
            100                 105                 110

<210> SEQ ID NO 33
<211> LENGTH: 112
<212> TYPE: PRT
<213> ORGANISM: Artificial
<220> FEATURE:
<223> OTHER INFORMATION: synthetic construct

<400> SEQUENCE: 33

Asp Ile Val Met Thr Gln Ser Pro Leu Ser Leu Pro Val Thr Pro Gly
1               5                   10                  15

Glu Pro Ala Ser Ile Ser Cys Arg Ser Ser Asp Ser Leu Gly His Ser
            20                  25                  30

Ser Gly Phe Thr Tyr Leu Ser Trp Tyr Leu Gln Lys Pro Gly Gln Ser
        35                  40                  45

Pro Gly Leu Leu Ile Tyr Lys Val Ser Asn Arg Phe Asp Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Leu Val Pro Trp Thr Phe Gly Gln Gly Thr Lys Leu Glu Ile Lys
            100                 105                 110

<210> SEQ ID NO 34
<211> LENGTH: 112
<212> TYPE: PRT
<213> ORGANISM: Artificial
<220> FEATURE:
<223> OTHER INFORMATION: synthetic construct

<400> SEQUENCE: 34

Asp Ile Val Met Thr Gln Ser Pro Leu Ser Leu Pro Val Thr Pro Gly
1               5                   10                  15
```

Glu Pro Ala Ser Ile Ser Cys Arg Ser Ser Asp Ser Leu Gly His Ser
            20                  25                  30

Thr Gly Phe Thr Tyr Leu Ser Trp Tyr Leu Gln Lys Pro Gly Gln Ser
        35                  40                  45

Pro Gly Leu Leu Ile Tyr Lys Val Ser Asn Arg Phe Asp Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Leu Val Pro Trp Thr Phe Gly Gln Gly Thr Lys Leu Glu Ile Lys
            100                 105                 110

<210> SEQ ID NO 35
<211> LENGTH: 112
<212> TYPE: PRT
<213> ORGANISM: Artificial
<220> FEATURE:
<223> OTHER INFORMATION: synthetic construct

<400> SEQUENCE: 35

Asp Ile Val Met Thr Gln Ser Pro Leu Ser Leu Pro Val Thr Pro Gly
1               5                   10                  15

Glu Pro Ala Ser Ile Ser Cys Arg Ser Ser Asp Ser Leu Gly His Ser
            20                  25                  30

Thr Gly Phe Thr Tyr Leu Ser Trp Tyr Leu Gln Lys Pro Gly Gln Ser
        35                  40                  45

Pro Gly Leu Leu Ile Tyr Lys Val Ser Asn Arg Phe Asp Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Leu Val Pro Trp Thr Phe Gly Gln Gly Thr Lys Leu Glu Ile Lys
            100                 105                 110

<210> SEQ ID NO 36
<211> LENGTH: 112
<212> TYPE: PRT
<213> ORGANISM: Artificial
<220> FEATURE:
<223> OTHER INFORMATION: synthetic construct

<400> SEQUENCE: 36

Asp Ile Val Met Thr Gln Ser Pro Leu Ser Leu Pro Val Thr Pro Gly
1               5                   10                  15

Glu Pro Ala Ser Ile Ser Cys Arg Ser Ser Asp His Leu Gly His Ser
            20                  25                  30

Thr Gly Tyr Thr Tyr Leu Ser Trp Tyr Leu Gln Lys Pro Gly Gln Ser
        35                  40                  45

Pro Gly Leu Leu Ile Tyr Lys Val Ser Asn Arg Phe Asp Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Leu Val Pro Trp Thr Phe Gly Gln Gly Thr Lys Leu Glu Ile Lys
            100                 105                 110

```
<210> SEQ ID NO 37
<211> LENGTH: 112
<212> TYPE: PRT
<213> ORGANISM: Artificial
<220> FEATURE:
<223> OTHER INFORMATION: synthetic construct

<400> SEQUENCE: 37

Asp Ile Val Met Thr Gln Ser Pro Leu Ser Leu Pro Val Thr Pro Gly
1               5                   10                  15

Glu Pro Ala Ser Ile Ser Cys Arg Ser Ser Asp Ser Leu Gly His Ser
            20                  25                  30

Ser Gly His Thr Tyr Leu Ser Trp Tyr Leu Gln Lys Pro Gly Gln Ser
        35                  40                  45

Pro Gly Leu Leu Ile Tyr Lys Val Ser Asn Arg Phe Asp Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Leu Val Pro Trp Thr Phe Gly Gln Gly Thr Lys Leu Glu Ile Lys
            100                 105                 110

<210> SEQ ID NO 38
<211> LENGTH: 112
<212> TYPE: PRT
<213> ORGANISM: Artificial
<220> FEATURE:
<223> OTHER INFORMATION: synthetic construct

<400> SEQUENCE: 38

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Gly His Ser
            20                  25                  30

Ser Gly His Thr Tyr Leu Ser Trp Tyr Leu Gln Lys Pro Gly Gln Ser
        35                  40                  45

Pro Gly Leu Leu Ile Tyr Lys Val Ser Asn Arg Phe Asp Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Leu Val Pro Trp Thr Phe Gly Gln Gly Thr Lys Leu Glu Ile Lys
            100                 105                 110

<210> SEQ ID NO 39
<211> LENGTH: 112
<212> TYPE: PRT
<213> ORGANISM: Artificial
<220> FEATURE:
<223> OTHER INFORMATION: synthetic construct

<400> SEQUENCE: 39

Asp Ile Val Met Thr Gln Ser Pro Leu Ser Leu Pro Val Thr Pro Gly
1               5                   10                  15

Glu Pro Ala Ser Ile Ser Cys Arg Ser Ser Asp Ser Leu Gly His Ser
            20                  25                  30

Ser Gly His Thr Tyr Leu Ser Trp Tyr Leu Gln Lys Pro Gly Gln Ser
        35                  40                  45
```

Pro Gly Leu Leu Ile Tyr Lys Val Ser Asn Arg Phe Asp Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr Leu Val Pro Trp Thr Phe Gly Gln Gly Thr Lys Leu Glu Ile Lys
            100                 105                 110

<210> SEQ ID NO 40
<211> LENGTH: 112
<212> TYPE: PRT
<213> ORGANISM: Artificial
<220> FEATURE:
<223> OTHER INFORMATION: synthetic construct

<400> SEQUENCE: 40

Asp Ile Val Met Thr Gln Ser Pro Leu Ser Leu Pro Val Thr Pro Gly
 1               5                  10                  15

Glu Pro Ala Ser Ile Ser Cys Arg Ser Ser Asp Ser Leu Gly His Ser
             20                  25                  30

Ser Gly His Thr Tyr Leu Ser Trp Tyr Leu Gln Lys Pro Gly Gln Ser
         35                  40                  45

Pro Gly Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr Leu Val Pro Trp Thr Phe Gly Gln Gly Thr Lys Leu Glu Ile Lys
            100                 105                 110

<210> SEQ ID NO 41
<211> LENGTH: 112
<212> TYPE: PRT
<213> ORGANISM: Artificial
<220> FEATURE:
<223> OTHER INFORMATION: synthetic construct

<400> SEQUENCE: 41

Asp Ile Val Met Thr Gln Ser Pro Leu Ser Leu Pro Val Thr Pro Gly
 1               5                  10                  15

Glu Pro Ala Ser Ile Ser Cys Arg Ser Ser Asp Ser Leu Gly His Ser
             20                  25                  30

Ser Gly His Thr Tyr Leu His Trp Tyr Leu Gln Lys Pro Gly Gln Ser
         35                  40                  45

Pro Gly Leu Leu Ile Tyr Lys Val Ser Asn Arg Phe Asp Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr Leu Val Pro Trp Thr Phe Gly Gln Gly Thr Lys Leu Glu Ile Lys
            100                 105                 110

<210> SEQ ID NO 42
<211> LENGTH: 112
<212> TYPE: PRT
<213> ORGANISM: Artificial

<220> FEATURE:
<223> OTHER INFORMATION: synthetic construct

<400> SEQUENCE: 42

Asp Ile Val Met Thr Gln Ser Pro Leu Ser Leu Pro Val Thr Pro Gly
1               5                   10                  15

Glu Pro Ala Ser Ile Ser Cys Arg Ser Ser Asp Ser Leu Gly His Ser
            20                  25                  30

Ser Gly His Thr Tyr Leu Ser Trp Tyr Leu Gln Lys Pro Gly Gln Ser
        35                  40                  45

Pro Gly Leu Leu Ile Tyr Lys Val Ser Asn Arg Phe Asp Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Leu Val Pro Trp Thr Phe Gly Gln Gly Thr Lys Leu Glu Ile Lys
            100                 105                 110

<210> SEQ ID NO 43
<211> LENGTH: 112
<212> TYPE: PRT
<213> ORGANISM: Artificial
<220> FEATURE:
<223> OTHER INFORMATION: synthetic construct

<400> SEQUENCE: 43

Asp Ile Val Met Thr Gln Ser Pro Leu Ser Leu Pro Val Thr Pro Gly
1               5                   10                  15

Glu Pro Ala Ser Ile Ser Cys Arg Ser Ser Asp Ser Leu Gly His Ser
            20                  25                  30

Asp Gly Asn Thr Tyr Leu Ser Trp Tyr Leu Gln Lys Pro Gly Gln Ser
        35                  40                  45

Pro Gly Leu Leu Ile Tyr Lys Val Ser Asn Arg Phe Asp Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr Leu Val Pro Trp Thr Phe Gly Gln Gly Thr Lys Leu Glu Ile Lys
            100                 105                 110

<210> SEQ ID NO 44
<211> LENGTH: 112
<212> TYPE: PRT
<213> ORGANISM: Artificial
<220> FEATURE:
<223> OTHER INFORMATION: synthetic construct

<400> SEQUENCE: 44

Asp Ile Val Met Thr Gln Ser Pro Leu Ser Leu Pro Val Thr Pro Gly
1               5                   10                  15

Glu Pro Ala Ser Ile Ser Cys Arg Ser Ser Asp Ser Leu Gly His Ser
            20                  25                  30

Ser Gly Asn Thr Tyr Leu Ser Trp Tyr Leu Gln Lys Pro Gly Gln Ser
        35                  40                  45

Pro Gly Leu Leu Ile Tyr Lys Val Ser Asn Arg Phe Asp Gly Val Pro
    50                  55                  60

Asp Arg Phe Ser Gly Ser Gly Ser Gly Thr Asp Phe Thr Leu Lys Ile

```
                65                  70                  75                  80
Ser Arg Val Glu Ala Glu Asp Val Gly Val Tyr Tyr Cys Ser Gln Ser
                    85                  90                  95
Thr Leu Val Pro Trp Thr Phe Gly Gln Gly Thr Lys Leu Glu Ile Lys
                100                 105                 110
```

<210> SEQ ID NO 45
<211> LENGTH: 116
<212> TYPE: PRT
<213> ORGANISM: Artificial
<220> FEATURE:
<223> OTHER INFORMATION: synthetic construct

<400> SEQUENCE: 45

```
Gln Val Gln Leu Val Gln Ser Gly Ala Glu Val Lys Lys Pro Gly Ala
1               5                   10                  15
Ser Val Lys Val Ser Cys Lys Val Ser Gly Tyr Thr Phe Thr Ser Thr
                20                  25                  30
Trp Met His Trp Val Arg Gln Ala Pro Gly Lys Gly Leu Glu Trp Met
            35                  40                  45
Gly Tyr Ile Asp Pro Ser Thr Gly Tyr Thr Glu Tyr Thr Gln Lys Phe
    50                  55                  60
Lys Asp Arg Val Thr Met Thr Glu Asp Thr Ser Thr Asp Thr Ala Tyr
65                  70                  75                  80
Met Glu Leu Ser Ser Leu Arg Ser Glu Asp Thr Ala Val Tyr Tyr Cys
                85                  90                  95
Ala Thr Asp Gly Tyr Asp Tyr Asp Tyr Trp Gly Gln Gly Thr Thr Val
                100                 105                 110
Thr Val Ser Ser
        115
```

<210> SEQ ID NO 46
<211> LENGTH: 116
<212> TYPE: PRT
<213> ORGANISM: Artificial
<220> FEATURE:
<223> OTHER INFORMATION: synthetic construct

<400> SEQUENCE: 46

```
Gln Val Gln Leu Val Gln Ser Gly Ala Glu Val Lys Lys Pro Gly Ala
1               5                   10                  15
Ser Val Lys Val Ser Cys Lys Val Ser Gly Tyr Thr Phe Thr Ser Thr
                20                  25                  30
Trp Met His Trp Val Arg Gln Ala Pro Gly Lys Gly Leu Glu Trp Met
            35                  40                  45
Gly Tyr Ile Asp Pro Ser Thr Gly Tyr Thr Glu Tyr Thr Gln Lys Phe
    50                  55                  60
Lys Asp Arg Val Thr Met Thr Glu Asp Thr Ser Thr Asp Thr Ala Tyr
65                  70                  75                  80
Met Glu Leu Ser Ser Leu Arg Ser Glu Asp Thr Ala Val Tyr Tyr Cys
                85                  90                  95
Ala Thr Asp Gly Tyr Asp Tyr Asp Tyr Trp Gly Gln Gly Thr Thr Val
                100                 105                 110
Thr Val Ser Ser
        115
```

<210> SEQ ID NO 47
<211> LENGTH: 116
<212> TYPE: PRT

-continued

```
<213> ORGANISM: Artificial
<220> FEATURE:
<223> OTHER INFORMATION: synthetic construct

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Thr
            20                  25                  30

Trp Met His Trp Val Arg Gln Ala Pro Gly Lys Gly Leu Glu Trp Met
        35                  40                  45

Gly Tyr Ile Asp Pro Ser Thr Gly Tyr Thr Glu Tyr Thr Gln Lys Phe
    50                  55                  60

Lys Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Gly Tyr Asp Phe Asp Tyr Trp Gly Gln Gly Thr Thr Val
            100                 105                 110

Thr Val Ser Ser
        115

<210> SEQ ID NO 48
<211> LENGTH: 116
<212> TYPE: PRT
<213> ORGANISM: Artificial
<220> FEATURE:
<223> OTHER INFORMATION: synthetic construct

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Thr
            20                  25                  30

Trp Met His Trp Val Arg Gln Ala Pro Gly Lys Gly Leu Glu Trp Met
        35                  40                  45

Gly Tyr Ile Asp Pro Ser Thr Gly Tyr Thr Glu Tyr Thr Gln Lys Phe
    50                  55                  60

Lys Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Gly Tyr Asp Phe Asp Tyr Trp Gly Gln Gly Thr Thr Val
            100                 105                 110

Thr Val Ser Ser
        115

<210> SEQ ID NO 49
<211> LENGTH: 116
<212> TYPE: PRT
<213> ORGANISM: Artificial
<220> FEATURE:
<223> OTHER INFORMATION: synthetic construct

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Thr
            20                  25                  30
```

Trp Met His Trp Val Arg Gln Ala Pro Gly Lys Gly Leu Glu Trp Met
            35                  40                  45

Gly Tyr Ile Asp Pro Ser Thr Gly Tyr Thr Glu Tyr Thr Gln Lys Phe
        50                  55                  60

Lys Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Gly Tyr Asp Tyr Asp Tyr Trp Gly Gln Gly Thr Thr Val
            100                 105                 110

Thr Val Ser Ser
        115

<210> SEQ ID NO 50
<211> LENGTH: 116
<212> TYPE: PRT
<213> ORGANISM: Artificial
<220> FEATURE:
<223> OTHER INFORMATION: synthetic construct

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Thr
            20                  25                  30

Trp Met His Trp Val Arg Gln Ala Pro Gly Lys Gly Leu Glu Trp Met
            35                  40                  45

Gly Tyr Ile Asp Pro Ser Thr Gly Tyr Thr Glu Tyr Thr Gln Lys Phe
        50                  55                  60

Lys Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Gly Tyr Asp Glu Asp Tyr Trp Gly Gln Gly Thr Thr Val
            100                 105                 110

Thr Val Ser Ser
        115

<210> SEQ ID NO 51
<211> LENGTH: 116
<212> TYPE: PRT
<213> ORGANISM: Artificial
<220> FEATURE:
<223> OTHER INFORMATION: synthetic construct

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Thr
            20                  25                  30

Trp Met His Trp Val Arg Gln Ala Pro Gly Lys Gly Leu Glu Trp Met
            35                  40                  45

Gly Tyr Ile Asp Pro Ser Thr Gly Tyr Thr Glu Tyr Thr Gln Lys Phe
        50                  55                  60

Lys Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Gly Tyr Asp Glu Asp Tyr Trp Gly Gln Gly Thr Thr Val
            100                 105                 110

Thr Val Ser Ser
        115

<210> SEQ ID NO 52
<211> LENGTH: 116
<212> TYPE: PRT
<213> ORGANISM: Artificial
<220> FEATURE:
<223> OTHER INFORMATION: synthetic construct

<400> SEQUENCE: 52

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Thr
            20                  25                  30

Trp Met His Trp Val Arg Gln Ala Pro Gly Lys Gly Leu Glu Trp Met
        35                  40                  45

Gly Tyr Ile Asn Pro Ser Thr Gly Tyr Thr Glu Tyr Thr Gln Lys Phe
    50                  55                  60

Lys Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Gly Tyr Asp Glu Asp Tyr Trp Gly Gln Gly Thr Thr Val
            100                 105                 110

Thr Val Ser Ser
        115

<210> SEQ ID NO 53
<211> LENGTH: 116
<212> TYPE: PRT
<213> ORGANISM: Artificial
<220> FEATURE:
<223> OTHER INFORMATION: synthetic construct

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Ser Thr
            20                  25                  30

Trp Met His Trp Val Arg Gln Ala Pro Gly Lys Gly Leu Glu Trp Met
        35                  40                  45

Gly Tyr Ile Asp Pro Ser Thr Gly Tyr Thr Glu Tyr Thr Gln Lys Phe
    50                  55                  60

Lys Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Gly Tyr Asp Glu Asp Tyr Trp Gly Gln Gly Thr Thr Val
            100                 105                 110

Thr Val Ser Ser
        115

<210> SEQ ID NO 54
<211> LENGTH: 116
<212> TYPE: PRT
<213> ORGANISM: Artificial
<220> FEATURE:

<223> OTHER INFORMATION: synthetic construct

<400> SEQUENCE: 54

```
Gln Val Gln Leu Val Gln Ser Gly Ala Glu Val Lys Lys Pro Gly Ala
1               5                   10                  15
Ser Val Lys Val Ser Cys Lys Val Ser Gly Tyr Thr Phe Thr Ser Thr
            20                  25                  30
Trp Met His Trp Val Arg Gln Ala Pro Gly Lys Gly Leu Glu Trp Met
        35                  40                  45
Gly Tyr Ile Asp Pro Ser Thr Gly Tyr Thr Glu Tyr Thr Gln Lys Phe
    50                  55                  60
Lys Asp Arg Val Thr Met Thr Glu Asp Thr Ser Thr Asp Thr Ala Tyr
65                  70                  75                  80
Met Glu Leu Ser Ser Leu Arg Ser Glu Asp Thr Ala Val Tyr Tyr Cys
                85                  90                  95
Ala Thr Asp Gly Tyr Asp Glu Asp Tyr Trp Gly Gln Gly Thr Thr Val
            100                 105                 110
Thr Val Ser Ser
        115
```

<210> SEQ ID NO 55
<211> LENGTH: 116
<212> TYPE: PRT
<213> ORGANISM: Artificial
<220> FEATURE:
<223> OTHER INFORMATION: synthetic construct

<400> SEQUENCE: 55

```
Gln Val Gln Leu Val Gln Ser Gly Ala Glu Val Lys Lys Pro Gly Ala
1               5                   10                  15
Ser Val Lys Val Ser Cys Lys Val Ser Gly Tyr Thr Phe Thr Ser Tyr
            20                  25                  30
Trp Met His Trp Val Arg Gln Ala Pro Gly Lys Gly Leu Glu Trp Met
        35                  40                  45
Gly Tyr Ile Asp Pro Ser Thr Gly Tyr Thr Glu Tyr Thr Gln Lys Phe
    50                  55                  60
Lys Asp Arg Val Thr Met Thr Glu Asp Thr Ser Thr Asp Thr Ala Tyr
65                  70                  75                  80
Met Glu Leu Ser Ser Leu Arg Ser Glu Asp Thr Ala Val Tyr Tyr Cys
                85                  90                  95
Ala Thr Asp Gly Tyr Asp Glu Asp Tyr Trp Gly Gln Gly Thr Thr Val
            100                 105                 110
Thr Val Ser Ser
        115
```

<210> SEQ ID NO 56
<211> LENGTH: 116
<212> TYPE: PRT
<213> ORGANISM: Artificial
<220> FEATURE:
<223> OTHER INFORMATION: synthetic construct

<400> SEQUENCE: 56

```
Gln Val Gln Leu Val Gln Ser Gly Ala Glu Val Lys Lys Pro Gly Ala
1               5                   10                  15
Ser Val Lys Val Ser Cys Lys Val Ser Gly Tyr Thr Phe Thr Ser Thr
            20                  25                  30
Trp Met His Trp Val Arg Gln Ala Pro Gly Lys Gly Leu Glu Trp Met
        35                  40                  45
```

Gly Tyr Ile Asp Pro Ser Thr Gly Tyr Thr Glu Tyr Thr Gln Lys Phe
            50                  55                  60

Lys Asp Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                85                  90                  95

Ala Thr Asp Gly Tyr Asp Glu Asp Tyr Trp Gly Gln Gly Thr Thr Val
                100                 105                 110

Thr Val Ser Ser
        115

<210> SEQ ID NO 57
<211> LENGTH: 116
<212> TYPE: PRT
<213> ORGANISM: Artificial
<220> FEATURE:
<223> OTHER INFORMATION: synthetic construct

<400> SEQUENCE: 57

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Phe Thr Ser Thr
                20                  25                  30

Trp Met His Trp Val Arg Gln Ala Pro Gly Lys Gly Leu Glu Trp Met
            35                  40                  45

Gly Tyr Ile Asp Pro Ser Thr Gly Tyr Thr Glu Tyr Thr Gln Lys Phe
            50                  55                  60

Lys Asp Arg Val Thr Met Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                85                  90                  95

Ala Thr Asp Gly Tyr Asp Glu Asp Tyr Trp Gly Gln Gly Thr Thr Val
                100                 105                 110

Thr Val Ser Ser
        115

<210> SEQ ID NO 58
<211> LENGTH: 112
<212> TYPE: PRT
<213> ORGANISM: Artificial
<220> FEATURE:
<223> OTHER INFORMATION: synthetic construct

<400> SEQUENCE: 58

Asp Ala Val Met Thr Gln Ile Pro Leu Thr Leu Ser Val Thr Ile Gly
 1               5                  10                  15

Gln Pro Ala Ser Ile Ser Cys Arg Ser Ser Asp Ser Leu Gly His Ser
                20                  25                  30

Asn Gly Asn Thr Tyr Leu Ser Trp Tyr Leu Gln Lys Pro Gly Gln Ser
            35                  40                  45

Pro Lys Leu Leu Ile Tyr Lys Val Ser Asn Arg Phe Asp Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Thr Tyr Phe Cys Ser Gln Ser
                85                  90                  95

Thr Leu Val Pro Trp Thr Phe Gly Gly Gly Thr Lys Leu Glu Ile Lys
                100                 105                 110

```
<210> SEQ ID NO 59
<211> LENGTH: 116
<212> TYPE: PRT
<213> ORGANISM: Artificial
<220> FEATURE:
<223> OTHER INFORMATION: synthetic construct

<400> SEQUENCE: 59

Gln Val Gln Leu Gln Gln Ser Arg Ala Glu Leu Ala Lys Pro Gly Ala
1               5                   10                  15

Ser Val Lys Met Ser Cys Lys Ala Ser Gly Tyr Thr Phe Thr Ser Thr
            20                  25                  30

Trp Met His Trp Val Lys Gln Gly Pro Gly Gln Gly Leu Glu Trp Ile
        35                  40                  45

Gly Tyr Ile Asp Pro Ser Thr Gly Tyr Thr Glu Tyr Thr Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Thr Asp Gly Tyr Asp Tyr Asp Tyr Trp Gly Gln Gly Thr Thr Leu
            100                 105                 110

Thr Val Ser Ser
        115

<210> SEQ ID NO 60
<211> LENGTH: 105
<212> TYPE: PRT
<213> ORGANISM: Rattus sp.

<400> SEQUENCE: 60

Asp Ala Ala Pro Thr Val Ser Ile Phe Pro Pro Ser Thr Glu Gln Leu
1               5                   10                  15

Ala Thr Gly Gly Ala Ser Val Val Cys Leu Met Asn Asn Phe Tyr Pro
            20                  25                  30

Arg Asp Ile Ser Val Lys Trp Lys Ile Asp Gly Thr Glu Arg Arg Asp
        35                  40                  45

Gly Val Leu Asp Ser Val Thr Asp Gln Asp Ser Lys Asp Ser Thr Tyr
    50                  55                  60

Ser Met Ser Ser Thr Leu Ser Leu Ser Lys Ala Asp Tyr Glu Ser His
65                  70                  75                  80

Asn Leu Tyr Thr Cys Glu Val Val His Lys Thr Ser Ser Ser Pro Val
                85                  90                  95

Val Lys Ser Phe Asn Arg Asn Glu Cys
            100                 105

<210> SEQ ID NO 61
<211> LENGTH: 324
<212> TYPE: PRT
<213> ORGANISM: Rattus sp.

<400> SEQUENCE: 61

Thr Thr Ala Pro Ser Val Tyr Pro Leu Ala Pro Gly Thr Ala Leu Lys
1               5                   10                  15

Ser Asn Ser Met Val Thr Leu Gly Cys Leu Val Lys Gly Tyr Phe Pro
            20                  25                  30

Glu Pro Val Thr Val Thr Trp Asn Ser Gly Ala Leu Ser Ser Gly Val
        35                  40                  45
```

```
His Thr Phe Pro Ala Val Leu Gln Ser Gly Leu Tyr Thr Leu Thr Ser
    50                  55                  60

Ser Val Thr Val Pro Ser Ser Thr Trp Pro Ser Gln Thr Val Thr Cys
65              70                  75                  80

Asn Val Ala His Pro Ala Ser Ser Thr Lys Val Asp Lys Lys Ile Val
                85                  90                  95

Pro Arg Asn Cys Gly Gly Asp Cys Lys Pro Cys Ile Cys Thr Gly Ser
            100                 105                 110

Glu Val Ser Ser Val Phe Ile Phe Pro Pro Lys Pro Lys Asp Val Leu
            115                 120                 125

Thr Ile Thr Leu Thr Pro Lys Val Thr Cys Val Val Val Asp Ile Ser
        130                 135                 140

Gln Asp Asp Pro Glu Val His Phe Ser Trp Phe Val Asp Asp Val Glu
145                 150                 155                 160

Val His Thr Ala Gln Thr Arg Pro Pro Glu Glu Gln Phe Asn Ser Thr
                165                 170                 175

Phe Arg Ser Val Ser Glu Leu Pro Ile Leu His Gln Asp Trp Leu Asn
            180                 185                 190

Gly Arg Thr Phe Arg Cys Lys Val Thr Ser Ala Ala Phe Pro Ser Pro
            195                 200                 205

Ile Glu Lys Thr Ile Ser Lys Pro Glu Gly Arg Thr Gln Val Pro His
210                 215                 220

Val Tyr Thr Met Ser Pro Thr Lys Glu Glu Met Thr Gln Asn Glu Val
225                 230                 235                 240

Ser Ile Thr Cys Met Val Lys Gly Phe Tyr Pro Pro Asp Ile Tyr Val
            245                 250                 255

Glu Trp Gln Met Asn Gly Gln Pro Gln Glu Asn Tyr Lys Asn Thr Pro
            260                 265                 270

Pro Thr Met Asp Thr Asp Gly Ser Tyr Phe Leu Tyr Ser Lys Leu Asn
            275                 280                 285

Val Lys Lys Glu Lys Trp Gln Gln Gly Asn Thr Phe Thr Cys Ser Val
        290                 295                 300

Leu His Glu Gly Leu His Asn His His Thr Glu Lys Ser Leu Ser His
305                 310                 315                 320

Ser Pro Gly Lys
```